United States Patent
Single et al.

(10) Patent No.: US 10,588,524 B2
(45) Date of Patent: Mar. 17, 2020

(54) METHOD AND APPARATUS FOR MEASUREMENT OF NEURAL RESPONSE

(75) Inventors: Peter Scott Vallack Single, Artarmon (AU); James Hamilton Laird, Artarmon (AU)

(73) Assignee: Saluda Medical Pty Ltd, Artarmon (AU)

( * ) Notice: Subject to any disclaimer, the term of this patent is extended or adjusted under 35 U.S.C. 154(b) by 60 days.

(21) Appl. No.: 14/117,153

(22) PCT Filed: May 11, 2012

(86) PCT No.: PCT/AU2012/000518
§ 371 (c)(1),
(2), (4) Date: Nov. 12, 2013

(87) PCT Pub. No.: WO2012/155190
PCT Pub. Date: Nov. 22, 2012

(65) Prior Publication Data
US 2014/0194772 A1    Jul. 10, 2014

(30) Foreign Application Priority Data

| | | | |
|---|---|---|---|
| May 13, 2011 | (AU) | ................................ | 2011901817 |
| May 13, 2011 | (AU) | ................................ | 2011901822 |
| May 13, 2011 | (AU) | ................................ | 2011901824 |

(51) Int. Cl.
*A61B 5/04* (2006.01)
*A61B 5/00* (2006.01)
(Continued)

(52) U.S. Cl.
CPC ............ *A61B 5/04001* (2013.01); *A61B 5/40* (2013.01); *A61B 5/4041* (2013.01);
(Continued)

(58) Field of Classification Search
CPC ............................ A61B 5/4041; A61N 1/0551
See application file for complete search history.

(56) References Cited

U.S. PATENT DOCUMENTS

| | | |
|---|---|---|
| 3,736,434 A | 5/1973 | Darrow |
| 3,817,254 A | 6/1974 | Maurer |

(Continued)

FOREIGN PATENT DOCUMENTS

| | | |
|---|---|---|
| EP | 0219084 | 4/1987 |
| EP | 0998958 B1 | 8/2005 |

(Continued)

OTHER PUBLICATIONS

Fagius et al. (Sympathetic Reflex Latencies and Conduction Velocities in Normal Man; 1980).*

(Continued)

*Primary Examiner* — Patrick Fernandes
(74) *Attorney, Agent, or Firm* — KPPB LLP

(57) ABSTRACT

A device for measuring a neural response evoked by a stimulus. First and second sense electrodes are positioned at distinct locations along a neural pathway. A neural stimulus is applied and first and second recordings of a neural response evoked by the stimulus are obtained from the respective sense electrodes. The first recording and the second recording are compared to determine propagation properties of the evoked neural response.

8 Claims, 16 Drawing Sheets

(51) Int. Cl.
*A61N 1/04* (2006.01)
*A61N 1/05* (2006.01)
*A61N 1/36* (2006.01)

(52) U.S. Cl.
CPC .............. *A61N 1/0456* (2013.01); *A61N 1/05* (2013.01); *A61N 1/0551* (2013.01); *A61N 1/36071* (2013.01); *A61N 1/36135* (2013.01)

(56) References Cited

U.S. PATENT DOCUMENTS

| | | | |
|---|---|---|---|
| 3,898,472 A | 8/1975 | Long | |
| 4,158,196 A * | 6/1979 | Crawford, Jr. | A61B 5/04282 |
| | | | 180/6.5 |
| 4,418,695 A | 12/1983 | Buffet | |
| 4,474,186 A | 10/1984 | Ledley et al. | |
| 4,628,934 A | 12/1986 | Pohndorf et al. | |
| 4,807,643 A | 2/1989 | Rosier | |
| 4,856,525 A | 8/1989 | Van et al. | |
| 5,113,859 A | 5/1992 | Funke | |
| 5,139,020 A | 8/1992 | Koestner et al. | |
| 5,143,081 A | 9/1992 | Young et al. | |
| 5,156,154 A | 10/1992 | Valenta, Jr. et al. | |
| 5,172,690 A | 12/1992 | Nappholz et al. | |
| 5,184,615 A | 2/1993 | Nappholz et al. | |
| 5,188,106 A | 2/1993 | Nappholz et al. | |
| 5,215,100 A * | 6/1993 | Spitz | A61B 5/4041 |
| | | | 600/554 |
| 5,324,311 A | 6/1994 | Acken | |
| 5,417,719 A | 5/1995 | Hull et al. | |
| 5,431,693 A | 7/1995 | Schroeppel | |
| 5,458,623 A | 10/1995 | Lu et al. | |
| 5,476,486 A | 12/1995 | Lu et al. | |
| 5,497,781 A * | 3/1996 | Chen | A61B 5/04004 |
| | | | 600/546 |
| 5,638,825 A | 6/1997 | Yamazaki et al. | |
| 5,702,429 A | 12/1997 | King et al. | |
| 5,758,651 A | 6/1998 | Nygard et al. | |
| 5,776,170 A | 7/1998 | MacDonald et al. | |
| 5,785,651 A | 7/1998 | Kuhn et al. | |
| 5,792,212 A | 8/1998 | Weijand et al. | |
| 5,814,092 A | 9/1998 | King | |
| 5,913,882 A | 6/1999 | King | |
| 5,999,848 A | 12/1999 | Gord et al. | |
| 6,020,857 A | 2/2000 | Podger | |
| 6,027,456 A | 2/2000 | Feler et al. | |
| 6,038,480 A | 3/2000 | Hrdlicka et al. | |
| 6,066,163 A | 5/2000 | John | |
| 6,114,164 A | 9/2000 | Dennis et al. | |
| 6,144,881 A | 11/2000 | Hemming et al. | |
| 6,157,861 A | 12/2000 | Faltys et al. | |
| 6,212,431 B1 | 4/2001 | Hahn et al. | |
| 6,246,912 B1 | 6/2001 | Sluijter et al. | |
| 6,381,496 B1 | 4/2002 | Meadows et al. | |
| 6,463,328 B1 | 10/2002 | John | |
| 6,473,649 B1 | 10/2002 | Gryzwa et al. | |
| 6,473,653 B1 | 10/2002 | Schallhorn et al. | |
| 6,493,576 B1 | 12/2002 | Dankwart-Eder | |
| 6,522,932 B1 | 2/2003 | Kuzma | |
| 6,600,955 B1 | 7/2003 | Zierhofer et al. | |
| 6,658,293 B2 | 12/2003 | Vonk et al. | |
| 6,675,046 B2 | 1/2004 | Holsheimer | |
| 6,782,292 B2 | 8/2004 | Whitehurst | |
| 6,898,582 B2 | 5/2005 | Lange et al. | |
| 7,089,059 B1 | 8/2006 | Pless | |
| 7,171,261 B1 | 1/2007 | Litvak et al. | |
| 7,231,254 B2 | 6/2007 | DiLorenzo et al. | |
| 7,286,876 B2 | 10/2007 | Yonce et al. | |
| 7,412,287 B2 | 8/2008 | Yonce et al. | |
| 7,450,992 B1 * | 11/2008 | Cameron | A61N 1/0551 |
| | | | 607/46 |
| 7,734,340 B2 | 6/2010 | De | |
| 7,742,810 B2 | 6/2010 | Moffitt | |
| 7,792,584 B2 | 9/2010 | Van et al. | |
| 7,818,052 B2 | 10/2010 | Litvak et al. | |
| 7,831,305 B2 | 11/2010 | Gliner | |
| 7,835,804 B2 | 11/2010 | Fridman et al. | |
| 8,190,251 B2 | 5/2012 | Molnar et al. | |
| 8,224,459 B1 | 7/2012 | Pianca et al. | |
| 8,239,031 B2 | 8/2012 | Fried et al. | |
| 8,359,102 B2 | 1/2013 | Thacker et al. | |
| 8,494,645 B2 | 7/2013 | Spitzer | |
| 8,588,929 B2 | 11/2013 | Davis et al. | |
| 8,670,830 B2 | 3/2014 | Carlson et al. | |
| 8,886,323 B2 | 11/2014 | Wu et al. | |
| 9,155,892 B2 | 10/2015 | Parker et al. | |
| 9,302,112 B2 | 4/2016 | Bornzin et al. | |
| 9,381,356 B2 | 7/2016 | Parker et al. | |
| 9,386,934 B2 | 7/2016 | Parker et al. | |
| 9,974,455 B2 | 5/2018 | Parker et al. | |
| 10,206,596 B2 | 2/2019 | Single et al. | |
| 10,278,600 B2 | 5/2019 | Parker et al. | |
| 10,368,762 B2 | 8/2019 | Single | |
| 2002/0055688 A1 | 5/2002 | Katims | |
| 2002/0099419 A1 | 7/2002 | Ayal et al. | |
| 2002/0193670 A1 * | 12/2002 | Garfield | A61B 5/0444 |
| | | | 600/304 |
| 2003/0032889 A1 | 2/2003 | Wells | |
| 2003/0045909 A1 | 3/2003 | Gross et al. | |
| 2003/0139781 A1 | 7/2003 | Bradley et al. | |
| 2003/0195580 A1 | 10/2003 | Bradley et al. | |
| 2004/0088017 A1 | 5/2004 | Sharma et al. | |
| 2004/0122482 A1 | 6/2004 | Tung et al. | |
| 2004/0158298 A1 | 8/2004 | Gliner | |
| 2004/0225211 A1 | 11/2004 | Gozani et al. | |
| 2004/0254494 A1 | 12/2004 | Spokoyny et al. | |
| 2005/0010265 A1 | 1/2005 | Baru Fassio | |
| 2005/0017190 A1 | 1/2005 | Eversmann et al. | |
| 2005/0021104 A1 | 1/2005 | DiLorenzo | |
| 2005/0065427 A1 * | 3/2005 | Magill | A61N 1/3605 |
| | | | 600/407 |
| 2005/0070982 A1 | 3/2005 | Heruth et al. | |
| 2005/0075683 A1 | 4/2005 | Miesel et al. | |
| 2005/0101878 A1 | 5/2005 | Daly | |
| 2005/0113877 A1 | 5/2005 | Giardello et al. | |
| 2005/0137670 A1 | 6/2005 | Christopherson et al. | |
| 2005/0149154 A1 | 7/2005 | Cohen | |
| 2005/0192567 A1 | 9/2005 | Katims | |
| 2005/0203600 A1 | 9/2005 | Wallace | |
| 2005/0209655 A1 | 9/2005 | Bradley et al. | |
| 2005/0282149 A1 | 12/2005 | Kovacs et al. | |
| 2006/0009820 A1 | 1/2006 | Royle et al. | |
| 2006/0020291 A1 | 1/2006 | Gozani | |
| 2006/0135998 A1 | 6/2006 | Libbus et al. | |
| 2006/0195159 A1 | 8/2006 | Bradley et al. | |
| 2006/0212089 A1 | 9/2006 | Tass | |
| 2006/0217782 A1 | 9/2006 | Boveja et al. | |
| 2006/0264752 A1 | 11/2006 | Rubinsky et al. | |
| 2006/0287609 A1 | 12/2006 | Litvak et al. | |
| 2007/0021800 A1 | 1/2007 | Bradley et al. | |
| 2007/0073354 A1 | 3/2007 | Knudson et al. | |
| 2007/0100378 A1 | 5/2007 | Maschino | |
| 2007/0178579 A1 | 8/2007 | Ross et al. | |
| 2007/0185409 A1 | 8/2007 | Wu et al. | |
| 2007/0208394 A1 | 9/2007 | King et al. | |
| 2007/0225767 A1 | 9/2007 | Daly | |
| 2007/0244410 A1 | 10/2007 | Fridman | |
| 2007/0250120 A1 | 10/2007 | Flach et al. | |
| 2007/0255372 A1 | 11/2007 | Metzler et al. | |
| 2007/0282217 A1 | 12/2007 | McGinnis et al. | |
| 2007/0287931 A1 | 12/2007 | Dilorenzo | |
| 2008/0021292 A1 | 1/2008 | Stypulkowski | |
| 2008/0051647 A1 | 2/2008 | Wu et al. | |
| 2008/0064947 A1 | 3/2008 | Heruth et al. | |
| 2008/0077191 A1 | 3/2008 | Morrell | |
| 2008/0097529 A1 | 4/2008 | Parramon et al. | |
| 2008/0147155 A1 | 6/2008 | Swoyer | |
| 2008/0183076 A1 | 7/2008 | Witte | |
| 2008/0208304 A1 | 8/2008 | Zdravkovic et al. | |
| 2008/0234780 A1 | 9/2008 | Smith et al. | |
| 2008/0275527 A1 | 11/2008 | Greenberg et al. | |
| 2008/0294221 A1 | 11/2008 | Kilgore | |
| 2008/0300655 A1 * | 12/2008 | Cholette | A61N 1/0556 |
| | | | 607/60 |

(56) References Cited

U.S. PATENT DOCUMENTS

| | | | |
|---|---|---|---|
| 2009/0033486 A1 | 2/2009 | Costantino et al. | |
| 2009/0082691 A1* | 3/2009 | Denison | A61B 5/04004 600/544 |
| 2009/0157155 A1 | 6/2009 | Bradley | |
| 2009/0270957 A1 | 10/2009 | Pianca | |
| 2009/0287277 A1 | 11/2009 | Conn et al. | |
| 2009/0299214 A1 | 12/2009 | Wu et al. | |
| 2009/0306491 A1 | 12/2009 | Haggers | |
| 2010/0010388 A1 | 1/2010 | Panken et al. | |
| 2010/0058126 A1 | 3/2010 | Chang et al. | |
| 2010/0069835 A1 | 3/2010 | Parker | |
| 2010/0069996 A1* | 3/2010 | Strahl | A61B 5/04001 607/55 |
| 2010/0070007 A1 | 3/2010 | Parker | |
| 2010/0070008 A1 | 3/2010 | Parker | |
| 2010/0106231 A1 | 4/2010 | Torgerson | |
| 2010/0114237 A1 | 5/2010 | Giftakis et al. | |
| 2010/0114258 A1 | 5/2010 | Donofrio et al. | |
| 2010/0125313 A1 | 5/2010 | Lee et al. | |
| 2010/0125314 A1 | 5/2010 | Bradley et al. | |
| 2010/0145222 A1 | 6/2010 | Brunnett et al. | |
| 2010/0152808 A1 | 6/2010 | Boggs | |
| 2010/0179626 A1 | 7/2010 | Pilarski | |
| 2010/0191307 A1 | 7/2010 | Fang et al. | |
| 2010/0204748 A1 | 8/2010 | Lozano et al. | |
| 2010/0222844 A1 | 9/2010 | Troosters et al. | |
| 2010/0222858 A1 | 9/2010 | Meloy | |
| 2010/0249643 A1* | 9/2010 | Gozani | A61B 5/0488 600/554 |
| 2010/0249867 A1 | 9/2010 | Wanasek | |
| 2010/0258342 A1 | 10/2010 | Parker | |
| 2010/0262208 A1 | 10/2010 | Parker | |
| 2010/0262214 A1 | 10/2010 | Robinson | |
| 2010/0280570 A1 | 11/2010 | Sturm et al. | |
| 2010/0286748 A1 | 11/2010 | Midani et al. | |
| 2010/0331604 A1 | 12/2010 | Okamoto et al. | |
| 2010/0331926 A1 | 12/2010 | Lee et al. | |
| 2011/0004207 A1 | 1/2011 | Wallace et al. | |
| 2011/0021943 A1 | 1/2011 | Lacour et al. | |
| 2011/0028859 A1 | 2/2011 | Chian | |
| 2011/0087085 A1 | 4/2011 | Tsampazis et al. | |
| 2011/0093042 A1 | 4/2011 | Torgerson et al. | |
| 2011/0106100 A1 | 5/2011 | Bischoff | |
| 2011/0184488 A1 | 7/2011 | De et al. | |
| 2011/0204811 A1 | 8/2011 | Pollmann-retsch | |
| 2011/0224749 A1 | 9/2011 | Ben-David et al. | |
| 2011/0264165 A1 | 10/2011 | Molnar et al. | |
| 2011/0270343 A1 | 11/2011 | Buschman et al. | |
| 2011/0307030 A1 | 12/2011 | John | |
| 2011/0313310 A1 | 12/2011 | Tomita | |
| 2011/0313483 A1 | 12/2011 | Hincapie et al. | |
| 2012/0029377 A1 | 2/2012 | Polak | |
| 2012/0101552 A1 | 4/2012 | Lazarewicz et al. | |
| 2012/0109236 A1 | 5/2012 | Jacobson et al. | |
| 2012/0253423 A1 | 10/2012 | Youn et al. | |
| 2012/0277621 A1 | 11/2012 | Gerber et al. | |
| 2012/0277823 A1 | 11/2012 | Gerber et al. | |
| 2013/0053722 A1 | 2/2013 | Carlson et al. | |
| 2013/0060302 A1 | 3/2013 | Polefko et al. | |
| 2013/0172774 A1 | 7/2013 | Crowder et al. | |
| 2013/0289661 A1 | 10/2013 | Griffith et al. | |
| 2013/0289683 A1 | 10/2013 | Parker et al. | |
| 2014/0066803 A1 | 3/2014 | Choi | |
| 2014/0142447 A1 | 5/2014 | Takahashi et al. | |
| 2014/0194771 A1 | 7/2014 | Parker et al. | |
| 2014/0236042 A1 | 8/2014 | Parker et al. | |
| 2014/0236257 A1 | 8/2014 | Parker et al. | |
| 2014/0243926 A1 | 8/2014 | Carcieri | |
| 2014/0243931 A1 | 8/2014 | Parker et al. | |
| 2014/0276195 A1 | 9/2014 | Papay et al. | |
| 2014/0277250 A1 | 9/2014 | Su et al. | |
| 2014/0288551 A1 | 9/2014 | Bharmi et al. | |
| 2014/0288577 A1 | 9/2014 | Robinson et al. | |
| 2014/0296737 A1 | 10/2014 | Parker et al. | |
| 2014/0358024 A1 | 12/2014 | Nelson et al. | |
| 2015/0018699 A1 | 1/2015 | Zeng et al. | |
| 2015/0164354 A1 | 6/2015 | Parker et al. | |
| 2015/0174396 A1 | 6/2015 | Fisher et al. | |
| 2015/0238104 A1 | 8/2015 | Tass | |
| 2015/0238304 A1 | 8/2015 | Lamraoui | |
| 2015/0282725 A1 | 10/2015 | Single | |
| 2015/0313487 A1 | 11/2015 | Single | |
| 2015/0360031 A1 | 12/2015 | Bornzin et al. | |
| 2015/0374999 A1 | 12/2015 | Parker | |
| 2016/0166164 A1 | 6/2016 | Obradovic et al. | |
| 2016/0287126 A1 | 10/2016 | Parker et al. | |
| 2016/0287182 A1 | 10/2016 | Single | |
| 2017/0001017 A9 | 1/2017 | Parker et al. | |
| 2017/0049345 A1 | 2/2017 | Single | |
| 2017/0071490 A1 | 3/2017 | Parker et al. | |
| 2017/0135624 A1 | 5/2017 | Parker | |
| 2017/0216587 A1 | 8/2017 | Parker | |
| 2018/0110987 A1 | 4/2018 | Parker | |
| 2018/0117335 A1 | 5/2018 | Parker et al. | |
| 2018/0132747 A1 | 5/2018 | Parker et al. | |
| 2018/0132760 A1 | 5/2018 | Parker | |
| 2018/0133459 A1 | 5/2018 | Parker et al. | |
| 2018/0228391 A1 | 8/2018 | Parker et al. | |
| 2018/0228547 A1 | 8/2018 | Parker | |
| 2018/0229046 A1 | 8/2018 | Parker et al. | |
| 2018/0256052 A1 | 9/2018 | Parker et al. | |
| 2019/0168000 A1 | 6/2019 | Laird-wah | |
| 2019/0216343 A1 | 7/2019 | Single et al. | |

FOREIGN PATENT DOCUMENTS

| | | | |
|---|---|---|---|
| EP | 2019716 | A | 11/2007 |
| EP | 2243510 | A2 | 10/2010 |
| EP | 2443995 | A2 | 4/2012 |
| EP | 2707095 | A1 | 3/2014 |
| JP | 2012524629 | | 10/2012 |
| JP | 2013527784 | A | 7/2013 |
| JP | 2013536044 | A | 9/2013 |
| WO | 1983003191 | A | 9/1983 |
| WO | 1993001863 | A1 | 2/1993 |
| WO | 9612383 | A1 | 4/1996 |
| WO | 2000002623 | A1 | 1/2000 |
| WO | 2002036003 | A1 | 11/2001 |
| WO | 2002038031 | | 5/2002 |
| WO | 2002049500 | A2 | 6/2002 |
| WO | 2003082521 | A2 | 4/2003 |
| WO | 2003043690 | | 5/2003 |
| WO | 2003103484 | | 12/2003 |
| WO | 2004021885 | A1 | 3/2004 |
| WO | 2004103455 | | 12/2004 |
| WO | 2005032656 | A1 | 4/2005 |
| WO | 2005105202 | A1 | 11/2005 |
| WO | 2006091636 | A2 | 8/2006 |
| WO | 2007064936 | A1 | 6/2007 |
| WO | 2007127926 | A2 | 11/2007 |
| WO | 2007130170 | A1 | 11/2007 |
| WO | 2008004204 | A1 | 1/2008 |
| WO | 2008049199 | A1 | 5/2008 |
| WO | 2009002072 | A2 | 12/2008 |
| WO | 2009002579 | A1 | 12/2008 |
| WO | 2009010870 | A2 | 1/2009 |
| WO | 2009130515 | A2 | 10/2009 |
| WO | WO 2009130515 A2 * | | 10/2009 ........... A61N 1/0556 |
| WO | 2009146427 | A1 | 12/2009 |
| WO | 2010013170 | A1 | 2/2010 |
| WO | 2010044989 | A2 | 4/2010 |
| WO | 2010051392 | A1 | 5/2010 |
| WO | 2010057046 | A2 | 5/2010 |
| WO | 2010124139 | A1 | 10/2010 |
| WO | 2010138915 | A1 | 12/2010 |
| WO | 2011011327 | A1 | 1/2011 |
| WO | 2011066477 | A1 | 6/2011 |
| WO | 2011066478 | A1 | 6/2011 |
| WO | 2011112843 | A1 | 9/2011 |
| WO | 2011119251 | A2 | 9/2011 |
| WO | 2011159545 | A2 | 12/2011 |
| WO | 2012027252 | A2 | 3/2012 |
| WO | 2012027791 | A1 | 3/2012 |
| WO | 2012155183 | A1 | 11/2012 |

(56) References Cited

FOREIGN PATENT DOCUMENTS

| WO | 2012155184 A1 | 11/2012 |
|---|---|---|
| WO | 2012155185 A1 | 11/2012 |
| WO | 2012155187 A1 | 11/2012 |
| WO | 2012155188 A1 | 11/2012 |
| WO | 2012155189 A1 | 11/2012 |
| WO | 2012155190 A1 | 11/2012 |
| WO | 2013063111 A1 | 5/2013 |
| WO | 2013075171 A1 | 5/2013 |
| WO | 2014071445 A1 | 5/2014 |
| WO | 2014071446 A1 | 5/2014 |
| WO | 2014143577 A1 | 9/2014 |
| WO | 2015070281 A1 | 5/2015 |
| WO | 2015074121 A1 | 5/2015 |
| WO | 2015109239 A1 | 7/2015 |
| WO | 2015143509 A1 | 10/2015 |
| WO | 2015168735 A1 | 11/2015 |
| WO | 2016011512 | 1/2016 |
| WO | 2016077882 A1 | 5/2016 |
| WO | 2016090420 A1 | 6/2016 |
| WO | 2016090436 A1 | 6/2016 |
| WO | 2016115596 A1 | 7/2016 |
| WO | 2016161484 A2 | 10/2016 |
| WO | 2016191807 A1 | 12/2016 |
| WO | 2016191808 A1 | 12/2016 |
| WO | 2016191815 A1 | 12/2016 |
| WO | 2017173493 A1 | 10/2017 |
| WO | 2017219096 A1 | 12/2017 |

OTHER PUBLICATIONS

Extended European Search Report for EP Application 12785483.4, completed Sep 16, 2014, 7 pgs.
Kent et al., "Instrumentation to Record Evoked Potentials for Closed-Loop Control of Deep Brain Stimulation", Conf. Proc. IEEE Eng. Med Biol. Sol, Aug. 2012, 10 pgs.
European Search Report for European Application 12785619.3, Search Completed Oct. 13, 2014, dated Oct. 23, 2014, 7 pgs.
International Search Report for International Application No. PCT/AU2012/000511, International Filing Date May 11, 2012, Search Completed May 17, 2012, dated May 18, 2012, 4 pgs.
International Search Report for International Application No. PCT/AU2012/000512, International Filing Date May 11, 2012, Search Completed Jul. 10, 2012, dated Jul. 11, 2012, 4 pgs.
International Search Report for International Application No. PCT/AU2012/000513, International Filing Date May 11, 2012, Search Completed May 29, 2012, dated May 30, 2012, 5 pgs.
International Search Report for International Application No. PCT/AU2012/000515, International Filing Date May 11, 2012, Search Completed May 21, 2012, dated Jun. 4, 2012, 5 pgs.
International Search Report for International Application No. PCT/AU2012/000516, International Filing Date May 11, 2012, Search Completed Jul. 11, 2012, dated Jul. 12, 2012, 8 pgs.
International Search Report for International Application No. PCT/AU2012/000517, International Filing Date May 11, 2012, Search Completed Jun. 4, 2012, dated Jun. 6, 2012, 3 pgs.
International Search Report for International Application No. PCT/AU2012/000518, International Filing Date May 11, 2012, Search Completed Jun. 8, 2012, dated Jun. 12, 2012, 4 pgs.
Written Opinion for International Application No. PCT/AU2012/000511, International Filing Date May 11, 2012, Search Completed May 17, 2012, dated May 18, 2012, 5 pgs.
Written Opinion for International Application No. PCT/AU2012/000512, International Filing Date May 11, 2012, Search Completed Jul. 10, 2012, dated Jul. 11, 2012, 7 pgs.
Written Opinion for International Application No. PCT/AU2012/000513, International Filing Date May 11, 2012, Search Completed May 29, 2012, dated May 30, 2012, 7 pgs.
Written Opinion for International Application No. PCT/AU2012/000515, International Filing Date May 11, 2012, Search Completed May 21, 2012, dated Jun. 4, 2012, 4 pgs.
Written Opinion for International Application No. PCT/AU2012/000516, International Filing Date May 11, 2012, Search Completed Jul. 11, 2012, dated Jul. 12, 2012, 8 pgs.
Written Opinion for International Application No. PCT/AU2012/000517, International Filing Date May 11, 2012, Search Completed Jun. 4, 2012, dated Jun. 6, 2012, 5 pgs.
Written Opinion for International Application No. PCT/AU2012/000518, International Filing Date May 11, 2012, Search Completed Jun. 8, 2012, dated Jun. 12, 2012, 10 pgs.
European Search Report for European Application 12785669.8, Search Completed Sep. 22, 2014, dated Sep. 29, 2014, 5 pgs.
International Search Report for Australian Application 2011901829, Search Completed Feb. 6, 2012, dated Feb. 7, 2012, 3pgs.
Andreassen, S. et al., "Muscle Fibre Conduction Velocity in Motor Units of the Human Anterior Tibial Muscle: a New Size Principle Parameter", J. Physiol. (1987), 391, pp. 561-571.
Blum, A. R., "An Electronic System for Extracelluar Neural Stimulation and Recording", Dissertation, Georgia Institute of Technology, Aug. 2007, Retrieved from http://smartech.gatech.edu/handle/1853/16192 on Jan. 30, 2012.
Dawson, G. D., "The relative excitability and conduction velocity of sensory and motor nerve fibres in man", Journal of Physiology, 1956, vol. 131(2), pp. 436-451. Figs. 1-5; Table 1; p. 437 "Methods"; pp. 438-447 "Results."
Dijkstra, E. A., "Ultrasonic Distance Detection for a Closed-Loop Spinal Cord Stimulation System", Proceedings—19th International Conference—IEEE/EMBS Oct. 30-Nov. 2, 1997, Chicago, IL. p. 324 section 'Paraesthesia Coverage by Dermatome,' p. 326 section 'Total Paraesthesia Coverage' and Figures 1 and 6-10.
Dillier, N et al., "Measurement of the electrically evoked compound action potential via a neural response telemetry system", Ann. Otol. Rhinol. Laryngol. 111 (May 2002), No. 5, pp. 407-414. Abstract & Figures 2-3, 407-414.
Fagius, J. et al., "Sympathetic Reflex Latencies and Conduction Velocities in Normal Man", Journal of Neurological Sciences, 1980. vol. 47, pp. 433-448.
Goodall, E. V., "Modeling Study of Activation and Propagation delays During Stimulation of Peripheral Nerve Fibres with a Tripolar Cuff Electrode", IEEE Trans.Rehab.Eng. V. 3, pp. 272-282.
Harper, A. A., "Conduction Velocity is Related to Morphological Cell Type in Rat Dorsal Root Ganglion Neurones", J. Physiol. (1985), 359, pp. 31-46.
Mahnam, A et al., "Measurement of the current-distance relationship using a novel refractory interaction technique", J. Neural Eng. 6 (2009), pp. 036005 (published May 20, 2009) Abstract, Sec. 2.2 & Figure 2b, 036005.
Massachusetts Institute of Techn, "The Compound Action Potential of the Frog Sciatic Nerve", Quantitative Physiology: Cells and Tissues. Fall, 1999, Retrieved from http://umech.mit.edu/freeman/6.021J/2001/lab.pdf on May 22, 2012.
Mcgill, Kevin et al., "On the Nature and Elimination of Stimulus Artifact in Nerve Signals Evoked and Recorded Using Surface Electrodes", IEEE Transactions on Biomedical Engineering, vol. BME-29, No. 2, Feb. 1982, pp. 129-137.
Opsommer, E. et al., "Determination of Nerve Conduction Velocity of C-fibres in Humans from Thermal Thresholds to Contact Heat (Thermode) and from Evoked Brain Potentials to Radiant Heat (CO2 Laser)", Neurophysiologie Clinique 1999, vol. 29, pp. 411-422.
Parker, J. L., "Compound Action Potentials Recorded in the Human Spinal Cord During Neurostimulation for Pain Relief", Pain, vol. 153, 2012, pp. 593-601.
Roy, S. H., "Effects of Electrode Location on Myoelectric Conduction Velocity and Median Frequency Estimates", J. Appl. Physiol. 61 (4), 1986, pp. 1510-1517.
Tomas et al., "Dorsal Root Entry Zone (DREZ) Localization Using Direct Spinal Cord Stimulation Can Improve Results of the DREZ Thermocoagulation Procedure for Intractable Pain Relief", Pain, 2005, vol. 116, pp. 159-163.
Yearwood, T. L., "Pulse Width Programming in Spinal Cord Stimulation: a Clinical Study", Pain Physician. 2010. vol. 13, pp. 321-335.

(56) References Cited

OTHER PUBLICATIONS

Borg et al., "Conduction velocity and refractory period of single motor nerve fibres in antecedent poliomyelitis", Journal of Neurology, Neurosurgery, and Psychiatry, vol. 50, 1987, 443-446.
Orstavik, Kristin et al., "Pathological C-fibres in patients with a chronic painful condition", Brain (2003), 126, 567-578.
Yuan, S. et al., "Recording monophasic action potentials using a platinum-electrode ablation catheter", Europace. Oct. 2000; 2(4):312-9; Abstract.
Extended European Search Report for European Application No. 11820923.8, report completed Dec. 9, 2013, report dated Dec. 17, 2013, 6 pgs.
Extended European Search Report for European Application No. 13852669.4, Search completed Jun. 8, 2016, dated Jun. 22, 2016, 09 Pgs.
Extended European Search Report for European Application No. 14861553.7, Search completed Jun. 8, 2017, dated Jun. 19, 2017, 8 Pgs.
Extended European Search Report for European Application No. 14863597.2, Search completed Jun. 6, 2017, dated Jun. 13, 2017, 9 Pgs.
Extended European Search Report for European Application No. 13853514.1, Search completed Jun. 8, 2016, dated Jun. 15, 2016, 07 Pgs.
Extended European Search Report for European Application No. 15768956.3, Search completed Oct. 3, 2017, dated Oct. 10, 2017, 8 Pgs.
Kumar et al., "Double-blind evaluation of subthalamic nucleus deep brain stimulation in advanced Parkinson's disease", by the American Academy of Neurology, 51, No. 3, Sep. 1, 1998, pp. 850-855.
Kumar et al., "Globus Pallidus Deep Brain Stimulation for Generalized Dystonia: Clinical and PET Investigation", Neurology, 53, No. 4, 1999, pp. 871-874.
Laird et al., "A Model of Evoked Potentials in Spinal Cord Stimulation", IEEE Engineering in Medicine & Biology Society, 35th Annual Conference. Osaka, Japan: Jul. 3-7, 2013, pp. 6555-6558.
Lempka, Scott, "The Electrode-Tissue Interface During Recording and Stimulation in the Central Nervous System", published on May 2010.
Levy et al., "Incidence and Avoidance of Neurologic Complications with Paddle Type Spinal Cord Stimulation Leads", Neuromodulation 14(15), Sep. 2011, pp. 412-422.
Li et al., S., "Resonant antidromic cortical circuit activation as a consequence of high-frequency subthalamic deep-brain stimulation", J Neurophysiol. Dec. 2007; 98(6): 3525-37. First published Oct. 10, 2007. doi:10.1152/jn.00808.2007.
Ma et al., "Similar Electrophysiological Changes in Axotomized and Neighboring Intact Dorsal Root Ganglion Neurons", Journal of Neurophysiology 89, No. 3 (Mar. 1, 2003): 1588-1602, doi:10.1152/jn.00855.2002.
Macefield, "Spontaneous and Evoked Ectopic Discharges Recorded from Single Human Axons", Muscle & Nerve 21, No. 4, Apr. 1998, pp. 461-468.
Markandey, Vishal, "ECG Implementation on the TMS320C5515 DSP Medical Development Kit (MDK)", Texas Instruments Application Report Jun. 2010, 35 pgs.
Matzner et al., "Na+ Conductance and the Threshold for Repetitive Neuronal Firing", Brain Research 597, No. 1 (Nov. 27, 1992): 92-98, doi:10.1016/0006-8993(92)91509-D.
Melzack et al., "Pain mechanisms: a new theory", Science, New York, New York, vol. 150, No. 3699, Nov. 19, 1965, pp. 971-979.
Miles et al., "An Electrode for Prolonged Stimulation of the Brain", Proc. 8th Meeting World Soc. Stereotactic and Functional Neurosurgery, Part III, Zurich, 1981, Appl. Neurophysiol, 45, 1982, pp. 449-445.
Misawa et al., "Neuropathic Pain is Associated with Increased Nodal Persistent Na(+) Currents in Human Diabetic Neuropathy", Journal of the Peripheral Nervous System: JPNS, 14, No. 4 (Dec. 2009): 279-284.
Nordin et al., "Ectopic Sensory Discharges and Paresthesiae in Patients with Disorders of Peripheral Nerves, Dorsal Roots and Dorsal Columns", Pain 20, No. 3 (Nov. 1984): 231-245, doi:10.1016/0304-3959(84)90013-7.
Oakley et al., "Spinal Cord Stimulation: Mechanisms of Action", Spine 27, No. 22, Nov. 15, 2002, pp. 2574-2583.
Oakley et al., "Transverse Tripolar Spinal Cord Stimulation: Results of an International Multicenter Study", Neuromodulation, vol. 9, No. 3, 2006, pp. 192-203.
Obradovic et al., "Effect of pressure on the spinal cord during spinal cord stimulation in an animal model", Poster, 18th Annual Meeting of the North American Neuromodulation Society, Dec. 11-14, 2014, Las Vegas.
Oh et al., "Long-term hardware-related complications of deep brain stimulation", Neurosurgery, vol. 50, No. 6, Jun. 2002, pp. 1268-1274, discussion pp. 1274-1276.
Ouyang et al., "Compression Induces Acute Demyelination and Potassium Channel Exposure in Spinal Cord", Journal of Neurotrauma 27, No. 6, Jun. 2010, 1109-1120, doi:10.1089/neu.2010.1271.
Parker et al., "Closing the Loop in Neuromodulation Therapies: Spinal Cord Evoked Compound Action Potentials During Stimulation for Pain Management (230).", 2011, In 15th Annual Meeting, North American Neuromodulation Society (p. 48). Presented at the North American Neuromodulation Society, Las Vegas.
Parker et al., "Compound action potentials recorded in the human spinal cord during neurostimulation for pain relief", Pain, 2012, vol. 153, pp. 593-601.
Parker et al., "Electrically Evoked Compound Action Potentials Recorded From the Sheep Spinal Cord", Neuromodulation, vol. 16, 2013, pp. 295-303.
Penar et al., "Cortical Evoked Potentials Used for Placement of a Laminotomy Lead Array: A Case Report", Neuromodulation: Technology at the Neural Interface, accessed Apr. 19, 2011, doi:10.1111/j.1525-1403.2011.00352.x.
Richter et al., "EMG and SSEP Monitoring During Cervical Spinal Cord Stimulation", Journal of Neurosurgical Review 2011, Southern Academic Press, 1(S1), 2011, pp. 61-63.
Ridder et al., "Burst Spinal Cord Stimulation for Limb and Back Pain", World Neurosurgery, 2013, 9 pgs.
Ridder et al., "Burst Spinal Cord Stimulation toward Paresthesia-Free Pain Suppression", May 2010, vol. 66, pp. 986-990.
Schmidt et al., "Gating of tactile input from the hand", Exp Brain Res, 1990, 79, pp. 97-102.
Siegfried et al., "Bilateral Chronic Electrostimulation of Ventroposterolateral Pallidum: A New Therapeutic Approach for Alleviating all Parkinsonian Symptoms", Neurosurgery, 35, No. 6, Dec. 1994, pp. 1126-1130.
Siegfried et al., "Intracerebral Electrode Implantation System", Journal of Neurosurgery, vol. 59, No. 2, Aug. 1983, pp. 356-3591.
Srinivasan, S., "Electrode/Electrolyte Interfaces: Structure and Kinetics of Charge Transfer", Fuel Cells, 2006, Chapter 2, 67 Pages.
Struijk et al, "Paresthesia Thresholds in Spinal Cord Stimulation: A Comparison of Theoretical Results with Clinical Data", IEEE Transactions on Rehabilitation Engineering, vol. 1, No. 2, Jun. 1993, pp. 101-108.
Sufka et al., "Gate Control Theory Reconsidered", Brain and Mind, 3, No. 2, 2002, pp. 277-290.
Tamura et al., "Increased Nodal Persistent Na+ Currents in Human Neuropathy and Motor Neuron Disease Estimated by Latent Addition", Clinical Neurophysiology 117, No. 11 (Nov. 2006): 2451-2458, doi:10.1016/j.clinph.2006.07.309.
Tasker, "Deep Brain Stimulation is Preferable to Thalamotomy for Tremor Suppression", Surgical Neurology, 49, No. 2, 1998, pp. 145-153.
Taylor et al., "Spinal Cord Stimulation for Chronic Back and Leg Pain and Failed Back Surgery Syndrome: A Systematic Review and Analysis of Prognostic Factors", SPINE, vol. 30, No. 1, 2004, pp. 152-160.
Texas Instruments, "Precision, Low Power Instrumentation Amplifiers", Texas Instruments SBOS051B Oct. 1995, Revised Feb. 2005, 20 pgs.

(56) References Cited

OTHER PUBLICATIONS

Tscherter et al., "Spatiotemporal Characterization of Rhythmic Activity in Rat Spinal Cord Slice Cultures", European Journal of Neuroscience 14, No. 2 (2001), pp. 179-190.
Van Den Berg et al., "Nerve fiber size-related block of action currents by phenytoin in mammalian nerve", Epilepsia, Nov. 1994, 35(6), pp. 1279-1288.
Villavicencio, Alan T. "Laminectomy versus Percutaneous Electrode Placement for Spinal Cord Stimulation," Neurosurgery, vol. 46 (2), Feb. 2000, pp. 399-405.
Vleggeert et al., Lankamp, "Electrophysiology and morphometry of the Aalpha- and Abeta-fiber populations in the normal and regenerating rat sciatic nerve", Experimental Neurology, vol. 187, No. 2, Jun. 1, 2004, Available online Apr. 2, 2004, pp. 337-349.
Woessner, "Blocking Out the Pain, Electric Nerve Block Treatments for Sciatic Neuritis", Retrieved from: http://www.practicalpainmanagement.com/pain/spine/radiculopathy/blocking-out-pain, Last updated Jan. 10, 2012.
Wolter et al., "Effects of sub-perception threshold spinal cord stimulation in neuropathic pain: a randomized controlled double-blind crossover study", European Federation of International Association for the Study of Pain Chapters, 2012, pp. 648-655.
Wu et al., "Changes in Aβ Non-nociceptive Primary Sensory Neurons in a Rat Model of Osteoarthritis Pain", Molecular Pain 6, No. 1 (Jul. 1, 2010): 37, doi:10.1186/1744-8069-6-37.
Xie et al., "Functional Changes in Dorsal Root Ganglion Cells after Chronic Nerve Constriction in the Rat", Journal of Neurophysiology 73, No. 5 (May 1, 1995): 1811-1820.
Xie et al., "Sinusoidal Time-Frequency Wavelet Family and its Application in Electrograstrographic Signal Analysis", Proceedings of the 20th Annual International Conference of the IEEE Engineering in Medicine and Biology Society, vol. 20, No. 3, Oct. 29, 1998, pp. 1450-1453.
Yingling et al., "Use of Antidromic Evoked Potentials in Placement of Dorsal Cord Disc Electrodes", Applied Neurophysiology, 1986, vol. 49, pp. 36-41.
International Preliminary Report on Patentability for International Application No. PCT/AU2011/001127, Report dated Mar. 5, 2013, 9 pgs.
International Preliminary Report on Patentability for International Application No. PCT/AU2012/000511, Report dated Nov. 19, 2013, 6 pgs.
International Preliminary Report on Patentability for International Application No. PCT/AU2012/000512, Report dated Nov. 19, 2013, 8 pgs.
International Preliminary Report on Patentability for International Application No. PCT/AU2012/000513, Report dated Nov. 19, 2013, 11 pgs.
International Preliminary Report on Patentability for International Application No. PCT/AU2012/000515, Report dated Nov. 19, 2013, 5 pgs.
International Preliminary Report on Patentability for International Application No. PCT/AU2012/000516, Report dated Nov. 19, 2013, 9 pgs.
International Preliminary Report on Patentability for International Application No. PCT/AU2012/000517, Report dated Nov. 19, 2013, 6 pgs.
International Preliminary Report on Patentability for International Application No. PCT/AU2012/000518, Report dated Nov. 19, 2013, 11 pgs.
International Preliminary Report on Patentability for International Application No. PCT/AU2013/001279, Report dated May 12, 2015, 6 pgs.
International Preliminary Report on Patentability for International Application No. PCT/AU2013/001280, Report dated May 12, 2015, 6 pgs.
International Preliminary Report on Patentability for International Application No. PCT/AU2014/001049, Report dated May 17, 2016, 5 pgs.
International Preliminary Report on Patentability for International Application No. PCT/AU2014/050369, Report dated May 24, 2016, 8 pgs.
International Preliminary Report on Patentability for International Application No. PCT/AU2015/050135, Report dated Oct. 4, 2016, 13 pgs.
International Preliminary Report on Patentability for International Application No. PCT/AU2015/050215, Report dated Nov. 8, 2016, 4 pgs.
International Preliminary Report on Patentability for International Application No. PCT/AU2015/050422, Report dated Jan. 31, 2017, 8 pgs.
International Preliminary Report on Patentability for International Application No. PCT/AU2015/050724, Report dated May 23, 2017, 5 pgs.
International Preliminary Report on Patentability for International Application No. PCT/AU2015/050753, Report dated Jun. 13, 2017, 7 pgs.
International Preliminary Report on Patentability for International Application No. PCT/AU2015/050787, Report dated Jun. 13, 2017, 6 pgs.
International Preliminary Report on Patentability for International Application No. PCT/AU2016/050019, Report dated Jul. 25, 2017, 9 pgs.
International Preliminary Report on Patentability for International Application No. PCT/AU2016/050263, Report dated Oct. 10, 2017, 9 pgs.
International Search Report and Written Opinion for International Application No. PCT/AU2016/050263, Search completed Nov. 16, 2016, dated Nov. 16, 2016, 8 Pgs.
International Search Report and Written Opinion for International Application No. PCT/AU2016/050430, Search completed Aug. 16, 2016, dated Aug. 16, 2016, 10 Pgs.
International Search Report and Written Opinion for International Application No. PCT/AU2016/050431, Search completed Aug. 16, 2016, dated Aug. 16, 2016, 11 Pgs.
International Search Report and Written Opinion for International Application No. PCT/AU2016/050439, Search completed Jul. 15, 2016, dated Jul. 15, 2016, 8 Pgs.
Alam et al., "Evaluation of optimal electrode configurations for epidural spinal cord stimulation in cervical spinal cord injured rats", Journal of Neuroscience Methods, Mar. 2015, 28 pgs.
Fisher, "F-Waves—Physiology and Clinical Uses", TheScientificWorldJournal, (2007) 7, pp. 144-160.
Gad et al., "Development of a multi-electrode array for spinal cord epidural stimulation to facilitate stepping and standing after a complete spinal cord injury in adult rats", Journal of NeuroEngineering and Rehabilitation 2013, 10:2, 18 pgs.
Sayenko et al., "Neuromodulation of evoked muscle potentials induced by epidural spinal-cord stimulation in paralyzed individuals", Journal of Neurophysiology, vol. 111, No. 5, 2014, pp. 1088-1099, First published Dec. 11, 2013.
Struijk et al., "Excitation of Dorsal Root Fibers in Spinal Cord Stimulation: a Theoretical Study", IEEE Transactions on Biomedical Engineering, Jul. 1993, vol. 40, No. 7, pp. 632-639.
Yamada et al., "Extraction and Analysis of the Single Motor Unit F-Wave of the Median Nerve", EMG Methods for Evaluating Muscle and Nerve Function, InTech, 2012, 15 pgs.
International Type Search Report for International Application No. AU 2015902393, Search completed May 16, 2016, dated May 16, 2016, 8 Pgs.
International Preliminary Report on Patentability for International Application No. PCT/AU2012/001441, Report dated May 27, 2014, 10 pgs.
International Search Report & Written Opinion for International Application No. PCT/AU2013/001280, Search Completed Jan. 16, 2014, dated Jan. 16, 2014, 8 Pgs.
International Search Report & Written Opinion for International Application PCT/AU2013/001279, Search Completed Jan. 9, 2014, dated Jan. 9, 2014, 9 Pgs.
International Search Report and Written Opinion for International Application No. PCT/AU2011/001127, date completed Nov. 11, 2011, dated Nov. 15, 2011, 13 pgs.

(56) References Cited

OTHER PUBLICATIONS

International Search Report and Written Opinion for International Application No. PCT/AU2012/001441, International Filing Date Nov. 23, 2012, Search Completed Feb. 26, 2013, dated Feb. 26, 2013, 14 pgs.
International Search Report and Written Opinion for International Application No. PCT/AU2014/001049, Search completed Feb. 10, 2015, dated Feb. 10, 2015, 8 Pgs.
International Search Report and Written Opinion for International Application No. PCT/AU2014/050369, Search completed Feb. 20, 2015, dated Feb. 20, 2015, 14 Pgs.
International Search Report and Written Opinion for International Application No. PCT/AU2015/050135, Search completed Jun. 30, 2015, dated Jun. 30, 2015, 26 Pgs.
International Search Report and Written Opinion for International Application No. PCT/AU2015/050422, Search completed Oct. 14, 2015, dated Oct. 14, 2015, 17 Pgs.
International Search Report and Written Opinion for International Application No. PCT/AU2015/050724, Search completed May 9, 2016, dated May 9, 2016, 8 Pgs.
International Search Report and Written Opinion for International Application No. PCT/AU2015/050753, Search completed Feb. 10, 2016, dated Feb. 10, 2016, 10 Pgs.
International Search Report and Written Opinion for International Application No. PCT/AU2015/050787, Search completed Mar. 16, 2016, dated Mar. 16, 2016, 10 Pgs.
International Search Report and Written Opinion for International Application No. PCT/AU2016/050019, Search completed May 4, 2016, dated May 4, 2016, 16 Pgs.
International Search Report and Written Opinion for International Application No. PCT/AU2015/050215, Search completed Jul. 30, 2015, dated Jul. 30, 2015, 8 Pgs.
Medtronic, Spinal Cord Stimulation, RestoreSensor Neurostimulator, Features and Specification: Specification, Printed Jun. 16, 2014, 2 pgs.
Medtronic, Spinal Cord Stimulation, RestoreSensor Neurostimulator, Features and Specification: Summary Printed Jun. 16, 2014, 1 pg.
Medtronic, RestoreSensor Neurostimulator, Retrieved from: http://web.archive.org/web/20150328092923/http://professional.medtronic.com:80/pt/neuro/scs/prod/restore-sensor/features-specifications/index.htm, Capture Date Jul. 9, 2012, Printed on May 11, 2017.
"Advanced Pain Therapy using Neurostimulation for Chronic Pain", Medtronic RestoreSensor clinical trial paper, Clinical summary, Nov. 2011, pp. 32.
"Battelle Neurotechnology—Moving Beyond the Limits in Neurotechnology", Battelle, www.battelle.org, May 2014, pp. 1-2.
"Haptic technology", Wikipedia, Retrieved from: http://en.wikipedia.org/wiki/Haptic_technology, Last modified on Sep. 15, 2014, Printed on Sep. 15, 2014, 5 pgs.
"Implants for surgery, Cardiac pacemakers", IS-1 standard ISO 5841-3-2000, Oct. 15, 2000.
"Neural Bypass Technology Enables Movement in Paralyzed Patient", Posted on Jul. 29, 2014, 6 a.m. in Brain chips/computer interface, pp. 1-2.
"Spinal Cord Stimulation, About Spinal Cord Stimulation", Medtronic, Retrieved from: http://professional.medtronic.com/pt/neuro/scs/edu/about/index.htm, Printed on Jun. 16, 2014, 2 pgs.
"Wide bandwidth BioAmplifier", http://www.psylab.com/html/default_bioamp.htm, Printed Jan. 30, 2014, 1-3 pages.
Andy, "Parafascicular-Center Median Nuclei Stimulation for Intractable Pain and Dyskinesia (Painful-Dyskinesia)", Stereotactic and Functional Neurosurgery, Appl. Neurophysiol., 43, No. 3-5, 1980, pp. 133-144.
Balzer et al., "Localization of cervical and cervicomedullary stimulation leads for pain treatment using median nerve somatosensay evoked potential collision testing", Journal of Neurosurgery, Jan. 2011, vol. 114, No. 1: pp. 200-205.
Brown et al., "Impact of Deep Brain Stimulation on Upper Limb Askinesia in Parkinson's Disease", Annals of Neurology, 45, No. 4, 1999, pp. 473-488.
Budagavi et al., "Modelling of compound nerve action potentials health and disease", Engineering in Medicine and Biology Society, 1992 14th Annual International Conference of the IEEE. vol. 6. IEEE, 1992, pp. 2600-2601.
Coquery et al., "Backward and forward masking in the perception of cutaneous stimuli", Perception & Psychophysics, 1973, vol. 13.No. 2, pp. 161-163.
Devergnas et al., A., "Cortical potentials evoked by deep brain stimulation in the subthalamic area", Front Syst Neurosci. 2011; 5: 30. May 13, 2011. doi:10.3389/fnsys.2011.00030.
Doiron et al., "Persistent Na+ Current Modifies Burst Discharge by Regulating Conditional Backpropagation of Dendritic Spikes", Journal of Neurophysiology 89, No. 1 (Jan. 1, 2003): 324-337, doi:10.1152/jn.00729.2002.
England et al., "Increased Numbers of Sodium Channels Form Along Demyelinated Axons", Brain Research 548, No. 1-2 (May 10, 1991): 334-337.
Falowski et al., "Spinal Cord Stimulation: an update", Neurotherapeutics: The Journal of the American Society for Experimental NeuroTherapeutics 5, No. 1, Jan. 2008, pp. 86-99.
Franke et al., Felix, "An Online Spike Detection and Spike Classification Algorithm Capable of Instantaneous Resolution of Overlapping Spikes", Journal of Computational Neuroscience, 2010, vol. 29, No. 1-2, pp. 127-148.
Fuentes et al., "Spinal Cord Stimulation Restores Locomotion in Animal Models of Parkinson's Disease", Science, vol. 323, No. 5921, Mar. 20, 2009, pp. 1578-1582.
George et al., "Vagus nerve stimulation: a new tool for brain research and therapy", Biological Psychiatry 47, No. 4, Feb. 15, 2000, pp. 287-295.
Gorman et al., "ECAP Mapping of the Spinal Cord: Influence of Electrode Position on Aβ Recruitment", (2012). In 16th Annual Meeting. Presented at the North American Neuromodulation Society, Las Vegas, NV.
Gorman et al., "Neural Recordings for Feedback Control of Spinal Cord Stimulation: Reduction of Paresthesia Variability.", 2013,In International Neuromodulation Society 11th World Congress. Presented at the International Neuromodulation Society 11th World Congress, Berlin, Germany.
Hallstrom et al, "Distribution of lumbar spinal evoked potentials and their correlation with stimulation-induced paresthesiae", (1991), Electroencephalography and clinical neurophysiology 80:126-139.
Holsheimer et al., "Optimum Electrode Geometry for Spinal Cord Stimulation: the Narrow Bipole and Tripole", Medical and Biological Engineering and Computing, 35, No. 5, 1997, pp. 493-497.
Huff, Terry B. et al., "Real-Time CARS Imaging Reveals a Calpain-Dependent Pathway for Paranodal Myelin Retraction during High-Frequency Stimulation", PLoS ONE vol. 6, issue 3 (Mar. 3, 2011): e17176, 11 pgs.
Kent et al., AR, "Recording evoked potentials during deep brain stimulation: development and validation of instrumentation to suppress the stimulus artefact", J Neural Eng. Jun. 2012; 9 (3):036004, Apr. 18, 2012. doi: 10.1088/1741-2560/9/3/036004.
Kim et al., "A Wavelet-Based Method for Action Potential Detection From Extracellular Neural Signal Recording With Low Signal-to-Noise Ratio", IEEE Transactions on Biomedical Engineering, vol. 50. No. 8, Aug. 2003.
Kim et al., "Cell Type-specific Changes of the Membrane Properties of Peripherally-axotomized Dorsal Root Ganglion Neurons in a Rat Model of Neuropathic Pain", Neuroscience 86, No. 1 (May 21, 1998): 301-309, doi:10.1016/S0306-4522(98)00022-0.
Krames et al., "Neuromodulation", 1st Edition, Academic Press, 2009, p. 540-541.
Krarup, Christian, "Compound sensory action potential in normal and pathological human nerves", Muscle & nerve, vol. 29, No. 4 (2004), pp. 465-483.
Krishnan et al., "Excitability Differences in Lower-Limb Motor Axons During and After Ischemia", Muscle & nerve, vol. 31, No. 2 (2005), pp. 205-213.

(56) References Cited

OTHER PUBLICATIONS

Kumar et al., "Deep Brain Stimulation for Intractable Pain: a 15-year Experience", Neurosurgery, Issue 40, No. 4, Apr. 1997, pp. 736-747.
European Search Report for European Application No. 15861444.6, Search completed Jul. 13, 2018, dated Jul. 23, 2018, 8 pgs.
International Search Report and Written Opinion for International Application No. PCT/AU2017/050296, Search completed Jul. 28, 2017, dated Jul. 28, 2017, 10 pgs.
Partial European Search Report for European Application No. 16775966.1, Search completed Oct. 26, 2018, dated Nov. 6, 2018, 11 Pgs.
He et al., "Perception threshold and electrode position for spinal cord stimulation", Pain, 59 (1994) 55-63 pages.
Holsheimer et al., "Significance of the Spinal Cord Position in Spinal Cord Stimulation", Acta Neurochir (1995) [Suppl] 64: 119-124 pages.
Holsheimer et al., "Spinal Geometry and Paresthesia Coverage in Spinal Cord Stimulation", (1998 paper) 8 pages.
Olin et al., "Postural Changes in Spinal Cord Stimulation Perceptual Thresholds", Neuromodulation, vol. 1, No. 4, 1998, pp. 171-175.
Rattay, "Analysis of Models for External Stimulation of Axons", IEEE Transactions on Biomedical Engineering, vol. BME-33, No. 10, Oct. 1986, pp. 974-977.
Ross et al., "Improving Patient Experience with Spinal Cord Stimulation: Implications of Position-Related Changes in Neurostimulation", Neuromodulation 2011; e-pub ahead of print. DOI: 10.1111/j.1525-1403.2011.00407.x 6 pages.
Struijk, "The Extracellular Potential of a Myelinated Nerve Fiber in an Unbounded Medium and in Nerve Cuff Models", Biophysical Journal, vol. 72, Jun. 1997, pp. 2457-2469.
Extended European Search Report for European Application No. 16739680.3,.Search completed Jun. 1, 2018, dated Jun. 12, 2018, 9 Pgs.
Al-Ani et al., "Automatic removal of high-amplitude stimulus artefact from neuronal signal recorded in the subthalamic nucleus", Journal of Neuroscience Methods, vol. 198, Issue 1, 2011, pp. 135-146.
French et al., "Information transmission at 500 bits/s by action potentials in a mechanosensory neuron of the cockroach", Neuroscience Letters, vol. 243, No. 1-3, Feb. 1, 1998, pp. 113-116.
Herreras, "Local Field Potentials: Myths and Misunderstandings", Frontiers in Neural Circuits, Dec. 15, 2016, 16 pgs.
Extended European Search Report for European Application No. 16802237.4, Search completed Dec. 11, 2018, dated Dec. 19, 2018, 9 Pgs.
Extended European Search Report for European Application No. 16802238.2, Search completed Oct. 17, 2018, dated Oct. 24, 2018, 8 Pgs.
International Preliminary Report for International Application No. PCT/AU2017/050296, dated Oct. 9, 2018, 7 Pgs.
International Preliminary Report for International Application No. PCT/AU2017/050647, dated Dec. 25, 2018, 8 pgs.
International Search Report and Written Opinion for International Application No. PCT/AU2017/050647, Search completed Sep. 29, 2017, dated Sep. 29, 2017, 13 Pgs.
Bahmer et al., "Application of triphasic pulses with adjustable phase amplitude ratio (PAR) for cochlear ECAP recording: I. Amplitude growth functions", Journal of Neuroscience Methods, Clinical Neuroscience, 2012, vol. 205, pp. 202-211.
Bahmer et al., "Effects of electrical pulse polarity shape on intra cochlear neural responses in humans: Triphasic pulses with cathodic second phase", Hearing Research, 2013, vol. 306, pp. 123-130.
Gnadt et al., "Spectral Cancellation of Microstimulation Artifact for Simultaneous Neural Recording In Situ", IEEE Transactions on Biomedical Engineering, Oct. 2003, Date of Publication: Sep. 23, 2003, vol. 50, No. 10, pp. 1129-1135, DOI: 10.1109/TBME.2003.816077.
Jeffrey et al., "A reliable method for intracranial electrode implantation and chronic electrical stimulation in the mouse brain", BMC Neuroscience. Biomed Central. London. GB. vol. 14, No. 1, Aug. 6, 2013, p. 82.
Tronnier et al., "Magnetic Resonance Imaging with Implanted Neurostimulators: An In Vitro and In Vivo Study", Jan. 1999, Neurosurgery, vol. 44(1), p. 118-125.

\* cited by examiner

METHOD AND APPARATUS FOR MEASUREMENT OF NEURAL RESPONSE

CROSS-REFERENCE TO RELATED APPLICATIONS

This application is a national stage of Application No. PCT/AU2012/000518 filed May 11, 2012, which claims the benefit of Australian Provisional Patent Application No. 2011901824 filed May 13, 2011, Australian Provisional Patent Application No. 2011901817 filed May 13, 2011, and Australian Provisional Patent Application No. 2011901822 filed May 13, 2011, each of which are incorporated herein by reference.

TECHNICAL FIELD

The present invention relates to measurement of a neural response to a stimulus, and in particular relates to measurement of a compound action potential by using one or more electrodes implanted proximal to the neural pathway.

BACKGROUND OF THE INVENTION

There are a range of situations in which it is desirable to apply neural stimuli in order to give rise to a compound action potential (CAP). For example, neuromodulation is used to treat a variety of disorders including chronic pain, Parkinson's disease, and migraine. A neuromodulation system applies an electrical pulse to tissue in order to generate a therapeutic effect. When used to relieve chronic pain, the electrical pulse is applied to the dorsal column (DC) of the spinal cord. Such a system typically comprises an implanted electrical pulse generator, and a power source such as a battery that may be rechargeable by transcutaneous inductive transfer. An electrode array is connected to the pulse generator, and is positioned in the dorsal epidural space above the dorsal column. An electrical pulse applied to the dorsal column by an electrode causes the depolarisation of neurons, and generation of propagating action potentials. The fibres being stimulated in this way inhibit the transmission of pain from that segment in the spinal cord to the brain. To sustain the pain relief effects, stimuli are applied substantially continuously, for example at 100 Hz.

While the clinical effect of spinal cord stimulation (SCS) is well established, the precise mechanisms involved are poorly understood. The DC is the target of the electrical stimulation, as it contains the afferent Aβ fibres of interest. Aβ fibres mediate sensations of touch, vibration and pressure from the skin, and are thickly myelinated mechanoreceptors that respond to non-noxious stimuli. The prevailing view is that SCS stimulates only a small number of Aβ fibres in the DC. The pain relief mechanisms of SCS are thought to include evoked antidromic activity of Aβ fibres having an inhibitory effect, and evoked orthodromic activity of Aβ fibres playing a role in pain suppression. It is also thought that SCS recruits Aβ nerve fibres primarily in the DC, with antidromic propagation of the evoked response from the DC into the dorsal horn thought to synapse to wide dynamic range neurons in an inhibitory manner.

Neuromodulation may also be used to stimulate efferent fibres, for example to induce motor functions. In general, the electrical stimulus generated in a neuromodulation system triggers a neural action potential which then has either an inhibitory or excitatory effect. Inhibitory effects can be used to modulate an undesired process such as the transmission of pain, or to cause a desired effect such as the contraction of a muscle.

The action potentials generated among a large number of fibres sum to form a compound action potential (CAP). The CAP is the sum of responses from a large number of single fibre action potentials. The CAP recorded is the result of a large number of different fibres depolarising. The propagation velocity is determined largely by the fibre diameter, to which velocity is roughly proportional, and for large myelinated fibres found in the dorsal root entry zone (DREZ) and nearby dorsal column the velocity can be over 60 ms$^{-1}$. The CAP generated from the firing of a group of similar fibres is measured as a positive peak potential P1, then a negative peak N1, followed by a second positive peak P2. This is caused by the region of activation passing the recording electrode as the action potentials propagate along the individual fibres. An observed CAP signal will typically have a maximum amplitude in the range of microvolts, whereas a stimulus applied to evoke the CAP is typically several volts.

For effective and comfortable operation, it is necessary to maintain stimuli amplitude or delivered charge above a recruitment threshold, below which a stimulus will fail to recruit any neural response. It is also necessary to apply stimuli which are below a comfort threshold, above which uncomfortable or painful percepts arise due to increasing recruitment of Aδ fibres which are thinly myelinated sensory nerve fibres associated with acute pain, cold and pressure sensation. In almost all neuromodulation applications, a single class of fibre response is desired, but the stimulus waveforms employed can recruit other classes of fibres which cause unwanted side effects, such as muscle contraction if motor fibres are recruited. The task of maintaining appropriate neural recruitment is made more difficult by electrode migration and/or postural changes of the implant recipient, either of which can significantly alter the neural recruitment arising from a given stimulus, depending on whether the stimulus is applied before or after the change in electrode position or user posture. Postural changes alone can cause a comfortable and effective stimulus regime to become either ineffectual or painful.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect the present invention provides a method of measuring a neural response evoked by a stimulus, the method comprising:
  applying a neural stimulus
  making a first recording of a neural response evoked by the stimulus using a first sense electrode;

making a second recording of the neural response evoked by the stimulus using a second sense electrode spaced apart from the first electrode along a neural pathway of the neural response; and comparing the first recording and the second recording to determine propagation properties of the evoked response.

According to a second aspect the present invention provides a device for measuring a neural response evoked by a stimulus, the device comprising:

at least first and second sense electrodes which are configured to be positioned at distinct locations along a neural pathway; and a control unit configured to apply a neural stimulus, the control unit further configured to make a first recording of a neural response evoked by the stimulus using a first sense electrode, the control unit further configured to make a second recording of the neural response evoked by the stimulus using the second sense electrode; and the control unit further configured to compare the first recording and the second recording to determine propagation properties of the evoked neural response.

Some embodiments of the invention may provide for comparing the first recording and the second recording in order to gain information regarding a selected neural fibre class. In such embodiments, where the first and second electrode are a distance d apart and the selected neural fibre class has a conduction velocity of c, the first recording may be delayed by a time period $t=d/c$ before the comparing. Alternatively a time delay $t_n$ for each nth sense electrode may be individually estimated. For example the delays $t_n$ may be estimated in advance by obtaining measurements of a response evoked by a high amplitude stimuli, and/or by averaging $t_n$ estimates over multiple stimulus cycles, to provide improved signal to noise ratio in the estimates of $t_n$. The comparing may comprise summing together the first recording, delayed by t or $t_n$ as appropriate, and the second recording. Alternatively the comparing may comprise cross-correlating or convolving the delayed first recording with the second recording.

In some embodiments of the invention, more than two recordings may be obtained from respective electrodes spaced apart along the neural pathway, for example to further improve signal quality of the summation or convolution. Suitable delays applicable to the respective recordings can be determined from the electrode positions and conduction velocity of interest.

In further embodiments, the comparison may be performed for variable delays $t_i$, to yield a "propagram" reflecting the comparison outcome with respect to $t_i$. Should multiple fibre classes be recruited and making a contribution to the evoked neural response, such a propagram can be expected to have peaks at $t_i=d/c_i$, where the $c_i$ are the propagation velocity of each respective fibre class. The present invention thus permits the amplitude of each such peak in the propagram to be used as feedback to control a stimulus to provide desired selectivity of recruitment of each fibre class. Moreover, in such embodiments, the position of each peak $t_i$ in the propagram allows a measurement of the propagation velocity of each fibre class to be obtained, as $c_i=d/t_i$. The conduction velocity may be thus measured over time in order to diagnose a disease which affects the conduction velocity. Additionally or alternatively the position of a peak in the propagram may be used to obtain an estimate for the conduction velocity in order to estimate the delays $t_n$. The propagram may be produced in response to a high intensity stimulus, and or an average of measurements of responses evoked by multiple stimuli, in order to improve signal to noise ratio and improve the estimate of peak position in the propagram.

Additionally or alternatively, in some embodiments of the invention the plurality of recordings of the evoked neural response may be compared and combined in order to yield a single combined measurement having improved signal-to-noise ratio (SNR), which will tend to cancel decorrelated amplifier noise at each respective sense electrode. To compensate for neural response signal attenuation along the neural pathway, corresponding gain values may be applied to each of the plurality of measurements prior to combining. Moreover to compensate for dispersion of the neural signal along the neural pathway, corresponding phase terms may be applied to each of the plurality of measurements prior to the combining. Indeed, in general a filter matched to the expected response may be applied to each measurement obtained at each respective sense electrode, so that accumulating the respective filter output gives a measure of the amplitude of the response, with the benefit of coding gain.

In some embodiments, one sense electrode may be positioned caudally of the stimulus site, with another sense electrode being positioned rostrally of the stimulus site. In such embodiments, summing the signals sensed at each electrode will magnify the neural response signal while cancelling or attenuating stimulus artefact signals.

According to another aspect the present invention provides a computer program product comprising computer program code means to make a computer execute a procedure for measuring a neural response evoked by a stimulus, the computer program product comprising computer program code means for carrying out the method of the first aspect.

The neural response measurement obtained at each sense electrode may be conducted in accordance with the techniques set out in Daly (2007/0225767), the content of which is incorporated herein by reference. Additionally or alternatively, the neural response measurement may be conducted in accordance with the techniques set out in Nygard (U.S. Pat. No. 5,785,651), the content of which is incorporated herein by reference. Additionally or alternatively, the neural response measurement may be conducted in accordance with the techniques set out in the Australian provisional patent application No. 2011901817 in the name of National ICT Australia Ltd entitled "Method and apparatus for measurement of neural response" from which the present application claims priority.

BRIEF DESCRIPTION OF THE DRAWINGS

An example of the invention will now be described with reference to the accompanying drawings, in which.

DESCRIPTION OF THE PREFERRED EMBODIMENTS

Figure 1:
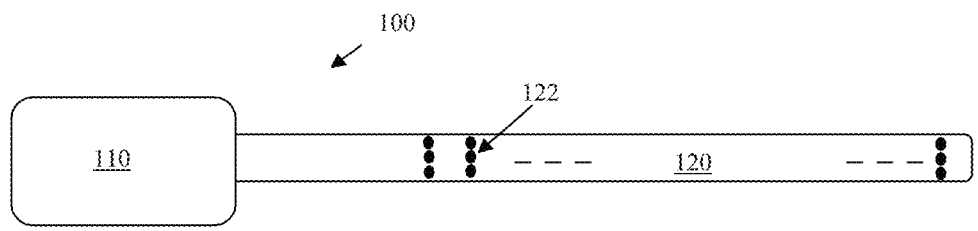
FIG. 1 illustrates an implantable device suitable for implementing the present invention.

FIG. 1 illustrates an implantable device 100 suitable for implementing the present invention. Device 100 comprises an implanted control unit 110, which controls application of neural stimuli, and controls a measurement process for obtaining a measurement of a neural response evoked by the stimuli from each of a plurality of electrodes. Device 100 further comprises an electrode array 120 consisting of a three by eight array of electrodes 122, each of which may be selectively used as either the stimulus electrode or sense electrode, or both.

During spinal cord stimulation, a current is injected into electrodes on the array near the spinal cord. This initiates action potentials in dorsal column nerve fibres underlying (i.e. immediately adjacent to) the point of stimulation. These action potentials then travel away from the point of initiation, in both directions.

Dorsal column nerve fibers enter the dorsal columns from the dorsal roots and then ascend to the brain. Spinal cord stimulation and measurement mainly interacts with those fibres that lie on or near the surface of the cord, which due to the anatomy of the cord are those fibres that have just entered the cord from a nearby dorsal root. These surface fibres are the most likely to be stimulated, and their action potentials are the largest contributors to evoked response measurements. For any given stimulation event, either a fibre is triggered, or it is not. As the amplitude of the evoked potential for a single fiber is invariant, the amplitude of the recorded compound action potential relates to how many fibers were triggered. The number of fibres triggered by a given stimulus can be controlled by varying the stimulation current. The action potential generated manifests itself as a current through the nerve's cell membrane at its nodes of Ranvier, which sets up a potential in the surrounding tissue. The amplitude of this potential field for a given fiber of fixed diameter is constant as it travels along. When measured at a point electrode near the fiber, the potential field has a characteristic time-varying 3-lobed shape, as the action potential first approaches and then recedes from the electrode.

An evoked SCP will usually contain the responses of different nerve fibre types. As discussed previously herein, the velocity of a neural response depends on the diameter of the fibre, and different fibre types have different diameters and different conduction velocities. Recorded signals of a single nerve response obtained from respective electrodes spaced apart along the array 120 are delayed with respect to each other due to the travelling nature of the action potentials. The amplitude also generally falls with distance away from the stimulus site, as a result of factors such as nerve fiber paths running deeper into the cord or into the dorsal roots away from the array, spatial effects whereby nearby bone structures and the like can vary the sensitivity of a recording electrode, and dispersion wherein different fibers have differences in propagation velocity, smearing the compound potential at greater distances from the stimulus.

The present embodiment recognises that these phenomena can be exploited to reduce the effect of electrical noise in an SCP measurement, and to preferentially amplify the response of a specific fibre class. The technique of this embodiment of the invention is shown in FIG. 2. The electrode array 202 is placed in the epidural space. In response to stimulation, an SCP 204 is induced, comprising the summed contributions of the various different fibre classes recruited. The SCP 204 travels along the neural pathway adjacent to the electrode array 202, with the contributions of the respective fibre classes travelling at respective velocities of $c_1, c_2, c_3 \ldots$. The distance between the electrodes in array 202 is d, and so the neural response components will respectively take a time of $t=d/c_i$ to pass between each electrode, where $c_i$ is the velocity of fibre class i. The signal from each electrode is amplified, and then delayed by an amount $n*t_i$ as shown, where n=0, 1, 2, 3 etc, and $t_i=d/c_i$. This creates a system that preferentially amplifies the SCP from action potentials travelling at the selected value of $c_i$, compared to signals arising from noise or signals arising from recruited nerves having a different conduction velocity. Effectively, this approach exploits the travelling nature of the signal across a number of electrodes to distinguish the signal from noise, which does not travel in this manner. The amplitude of the combined signal 206 can then be detected and used in a feedback loop, or for other purposes. The system of FIG. 2 provides the further benefit that the delayed sum will improve overall SNR, as the signals will be correlated but amplifier noise will not. This benefit can be significant due to the typical noise problems in chip amplifiers used in implants.

The inverse delay $t_i$ (or each such delay when not equal between each pair of adjacent electrodes) may be assumed to be proportional to electrode spacing, or may be established individually. For example an initial calibration recording may be made using a high stimulus amplitude, where the CEP amplitude is far above the noise levels. Recordings from different electrodes in response to the calibration stimulus can then be cross-correlated, and the optimal lags established between pairs of electrodes.

Figure 2A:
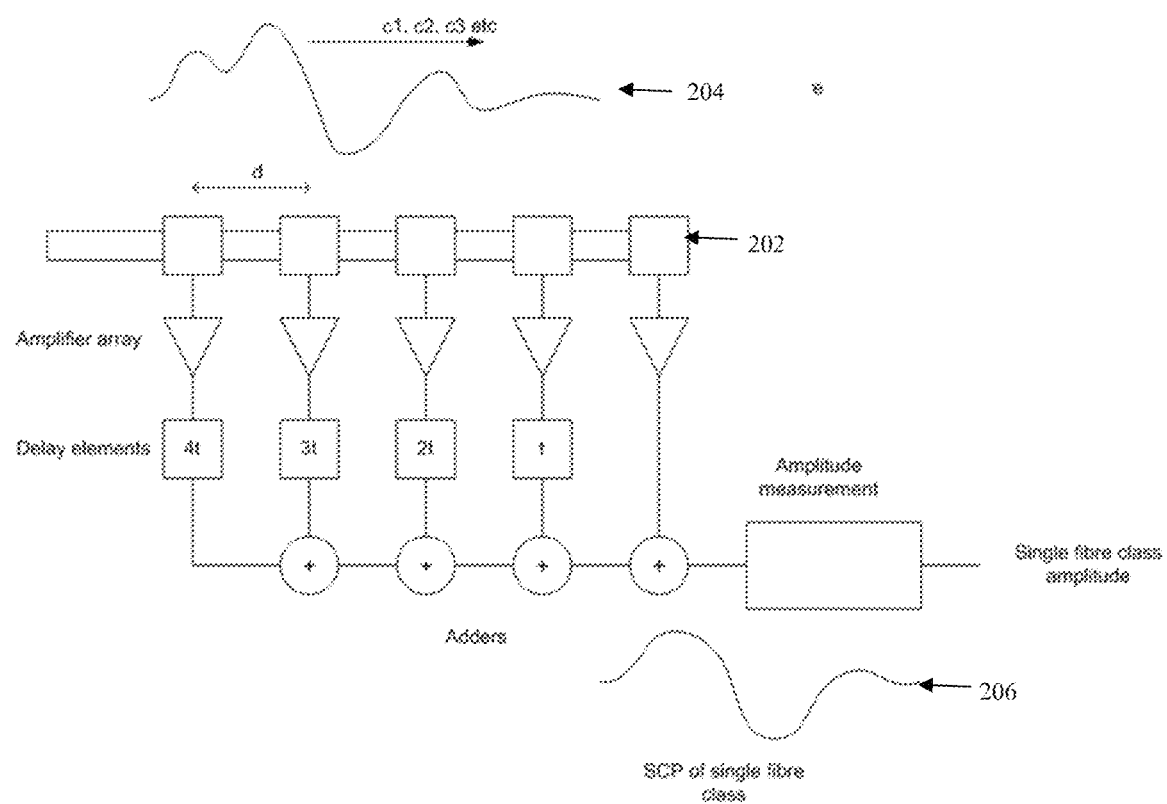
FIGS. 2a and 2b illustrate embodiments of the invention for selectively amplifying the neural response of a single fibre class.
Figure 2B:
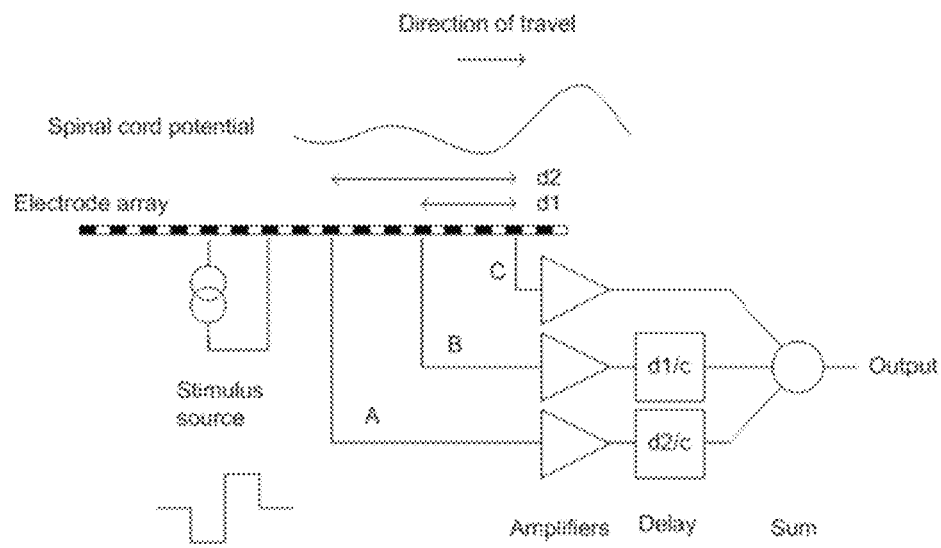

FIG. 2b illustrates another embodiment similar to that of FIG. 2a, configured for selectively amplifying the neural response of a single fibre class. In this embodiment the electrode spacing is not constant, and so the delay applied at each respective electrode is $d_i/c_i$, where the $d_i$ respectively are the distance from that electrode to the right-most measurement electrode shown in FIG. 2b. The stimulus, shown as a bi-phasic current pulse, elicits a response in the spinal cord (not shown). This initiates a response in the spinal cord, which travels away from the stimulating electrodes. It will be observed that the neural response arrives at electrode C last, and at electrode B at time $d_1/c$ earlier, (where c is the propagation speed of the potential in the tissue, typically 80 m/s or 1 ms for 8 cm) and A at a time $d_2/c$ earlier.

Figure 2C:
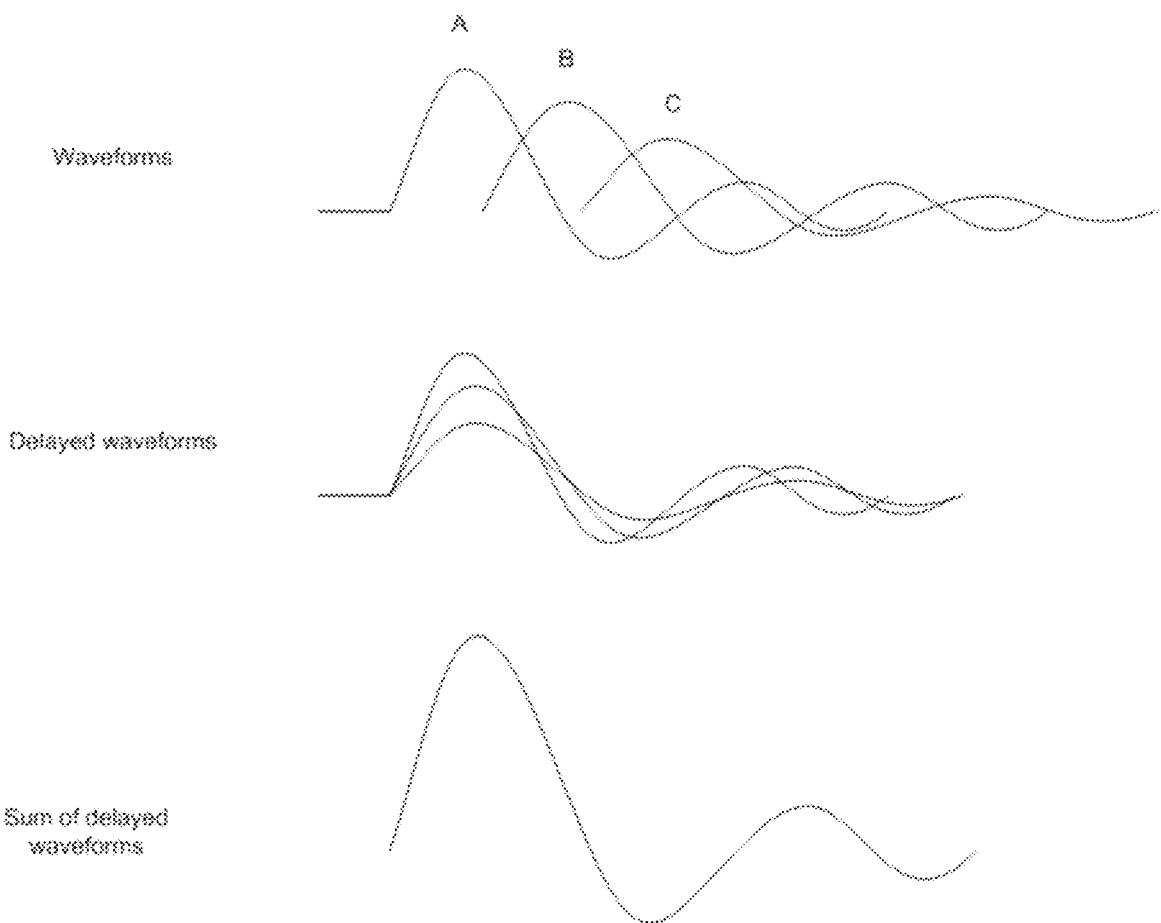
FIG. 2C illustrates sensed waveform alignment and summation.

FIG. 2c shows the way in which the delay elements of FIG. 2a or 2b can be used to align the sensed waveforms from the multiple electrodes, so that the waveforms' sum produces a larger output than that measured at any one electrode. Moreover, the signals received at the summing junction due to the SCP will be correlated, whereas the electrical noise from the amplifiers' front-end stages will not. Consequently, this will result in a net improvement of SNR of the summed output as compared to the individual amplifier outputs.

FIGS. 7 to 12 illustrate results obtained from experimental implementation of the concept shown in FIG. 2c. A linear array of 16 electrodes was established in a sheep's spine. Stimulus pulses were delivered with currents ranging from 100 μA to 600 μA using a tripolar configuration of electrodes at one end of the array, labelled electrodes 1 through 3. Evoked potentials were then recorded using electrodes 6 through 16. Each stimulus was delivered 200 times. The recordings used here consist of the differential voltages between successive electrodes.

For each electrode the recordings made in response to the stimulus at 600 µA were averaged, giving a low-noise signal. These are then upsampled by a factor of 10, in order to be able to estimate delays with sub-sample accuracy. The time of occurrence of the first negative peak was measured, and the difference between peak times of adjacent electrodes taken as the inter-electrode delay. In this way, for N electrodes, N-1 delays were obtained experimentally.

Figure 7B:
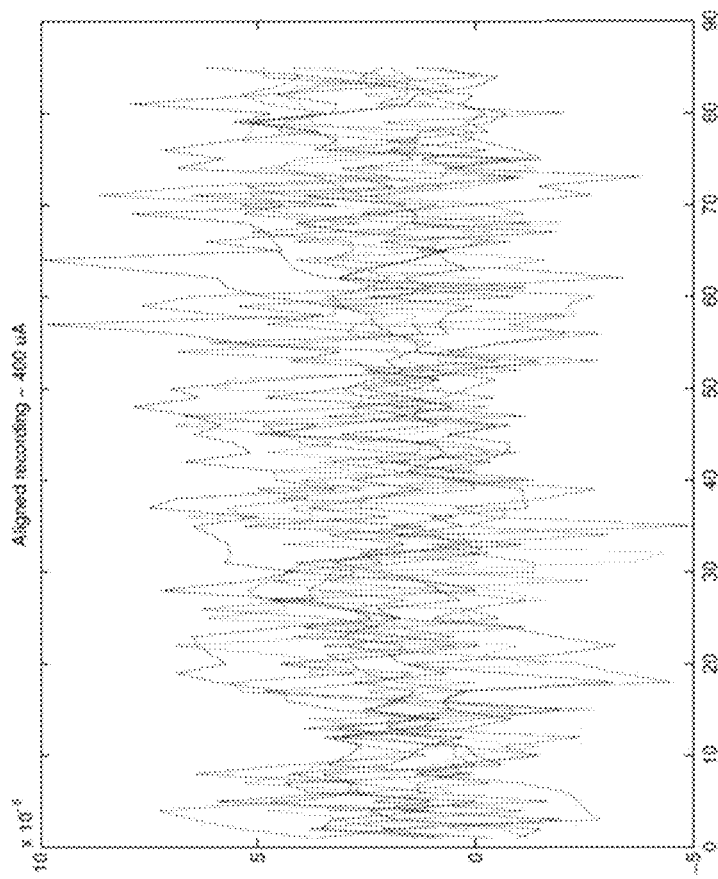
FIGS. 7 to 12 illustrate results obtained from experimental implementation of the concept shown in FIG. 2c.
Figure 7A:
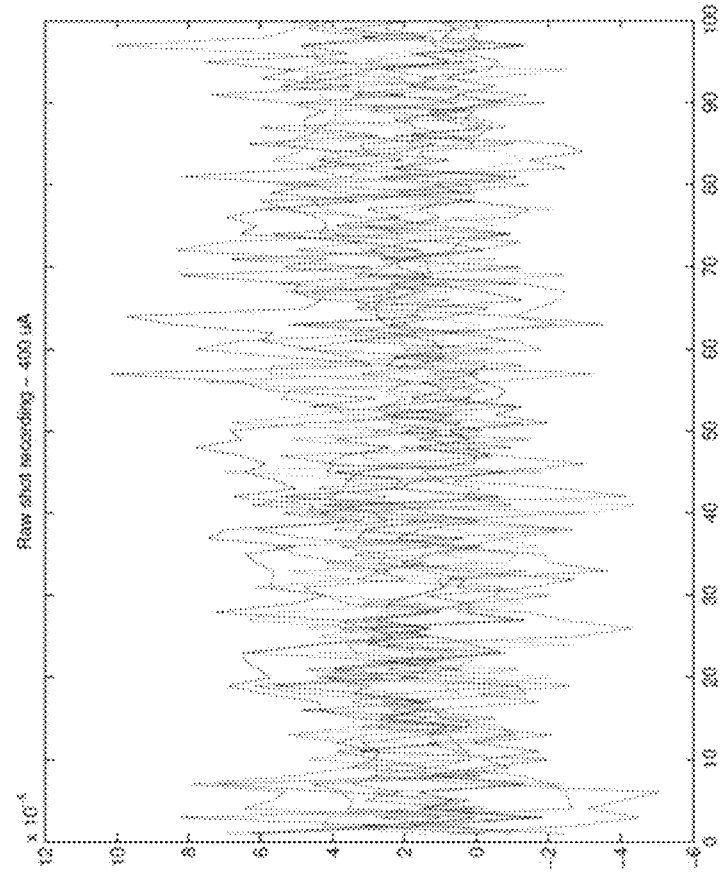
Figure 7C:
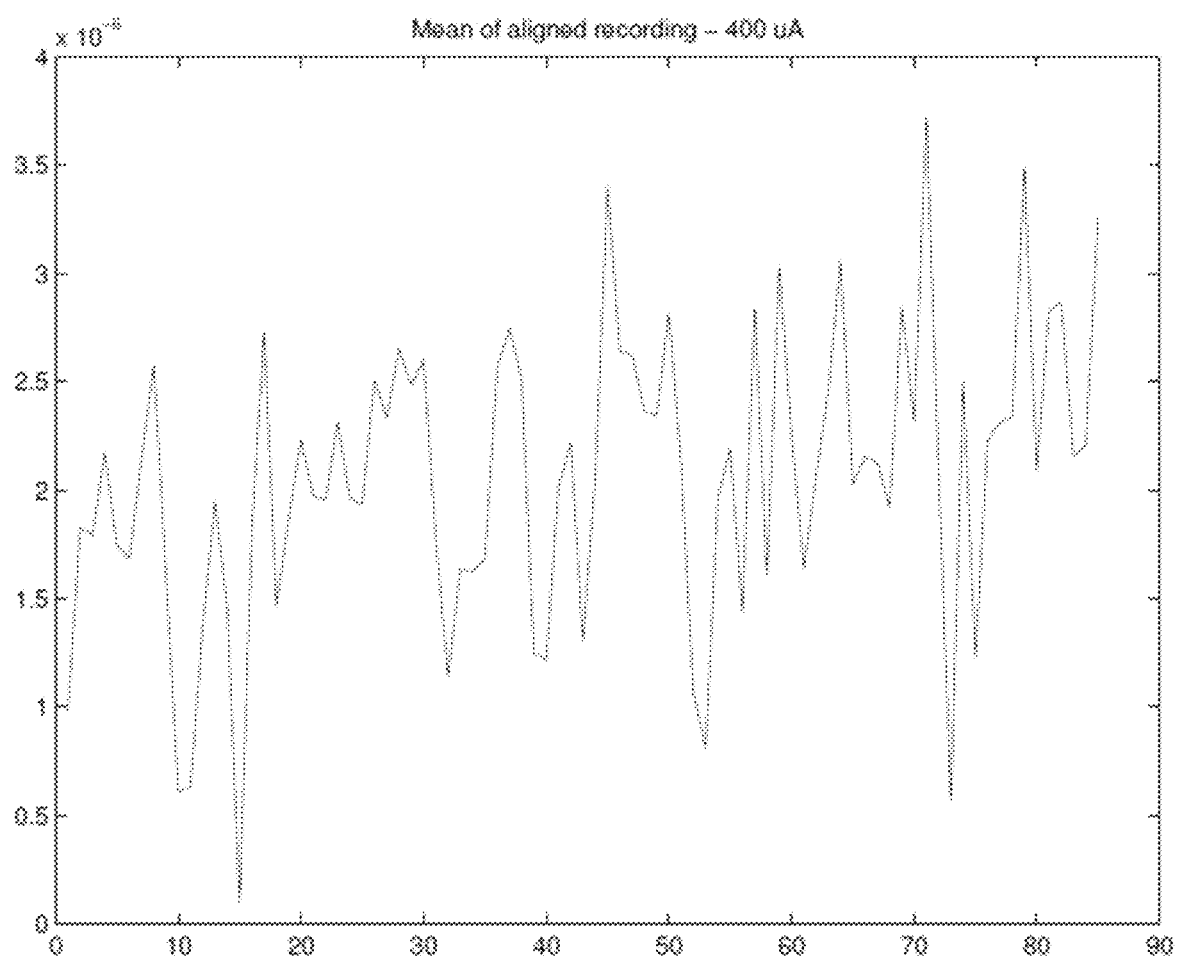

Recordings made at lower currents, shown in FIG. 7a, were then examined. Individual stimulus recordings were upsampled, and each recording channel was time-aligned with the other channels using the established delay values, to produce the time-shifted recordings shown in FIG. 7b. In this embodiment, the partially overlapped segments at the start and end of the recordings are discarded. In alternative embodiments these segments may be preserved but in further processing given less weight. The aligned recordings shown in FIG. 7b were then downsampled and averaged across the electrodes to obtain an aligned mean trace, as shown in FIG. 7c. The aligned mean trace can then be measured using any techniques normally applied to individual channels. A corresponding process was applied to the data of FIGS. 8a, 9a, 10a, 11a and 12a to derive FIGS. 8b, 9b, 10b, 11b and 12b, respectively, from which FIGS. 8c, 9c, 10c, 11c and 12c were respectively produced.

Figure 10B:
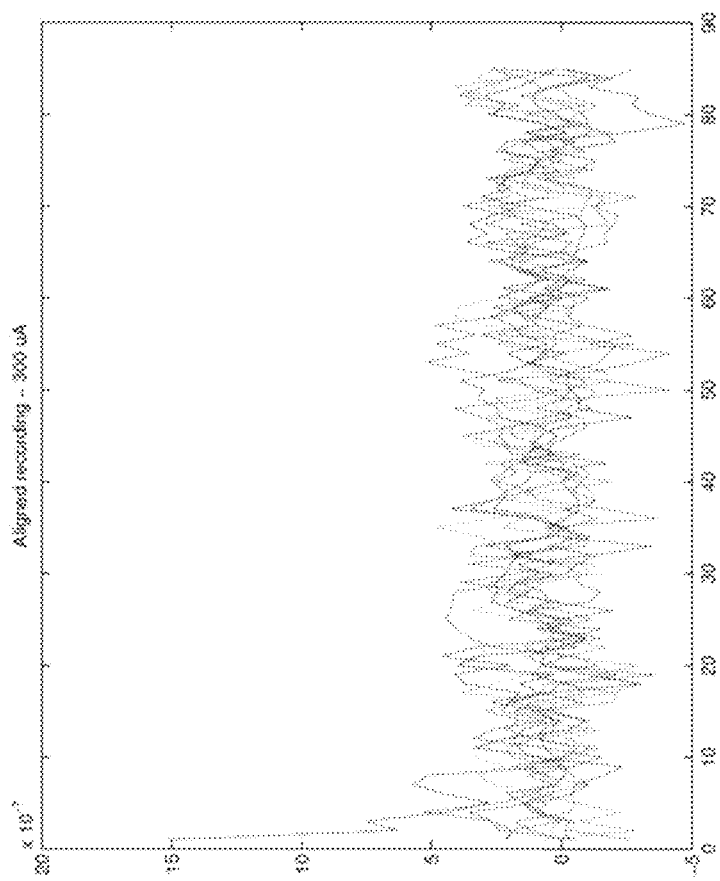
Figure 10A:
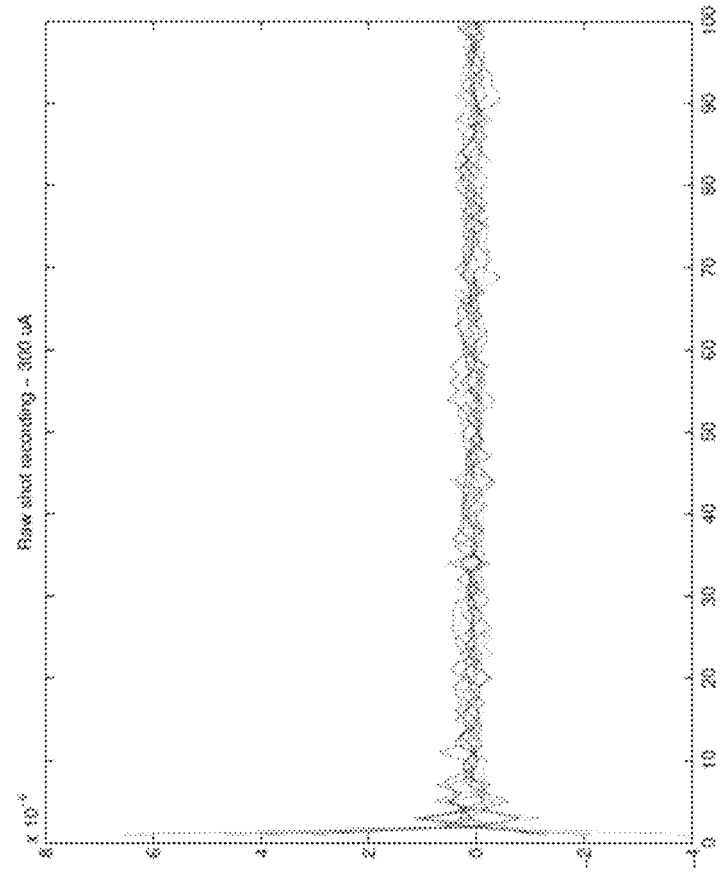
Figure 10C:
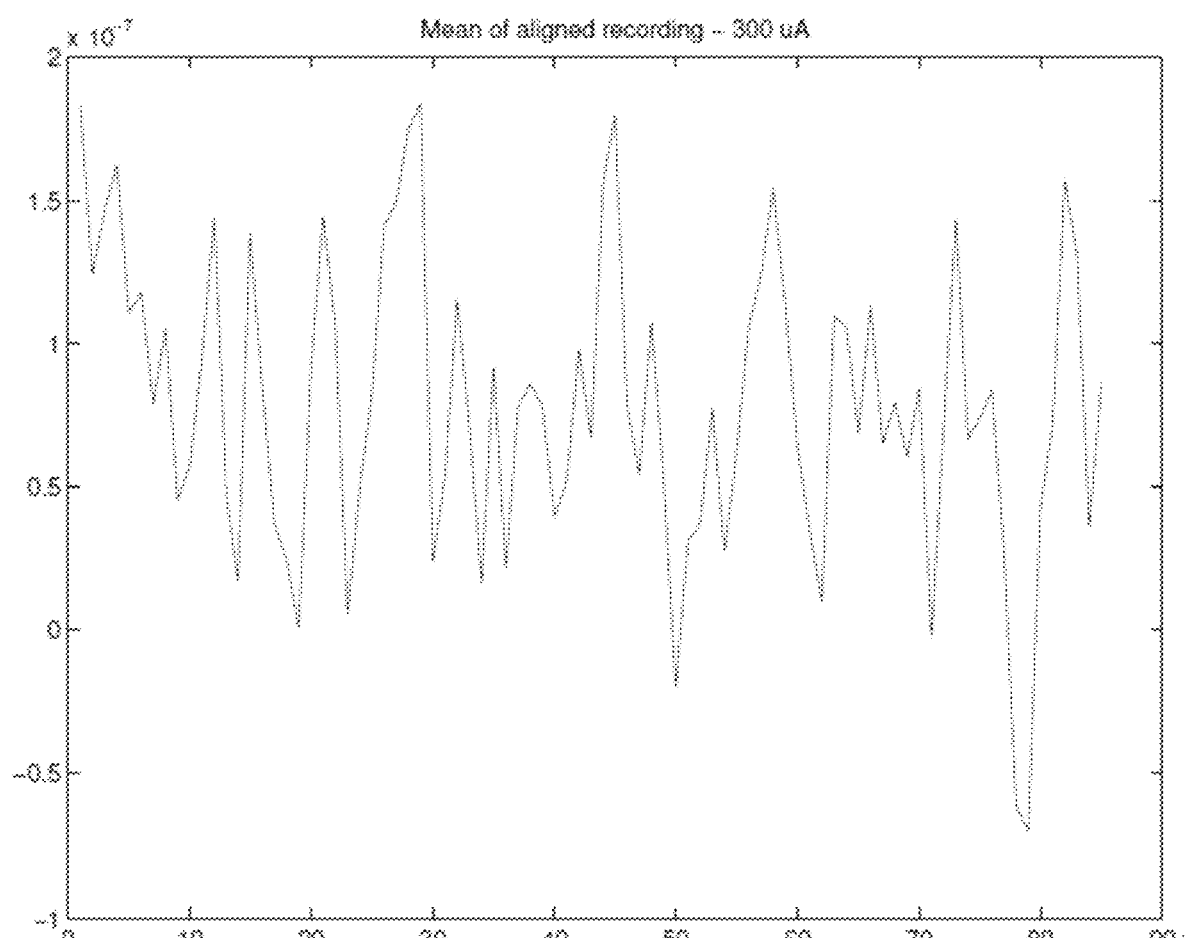
Figure 11A:
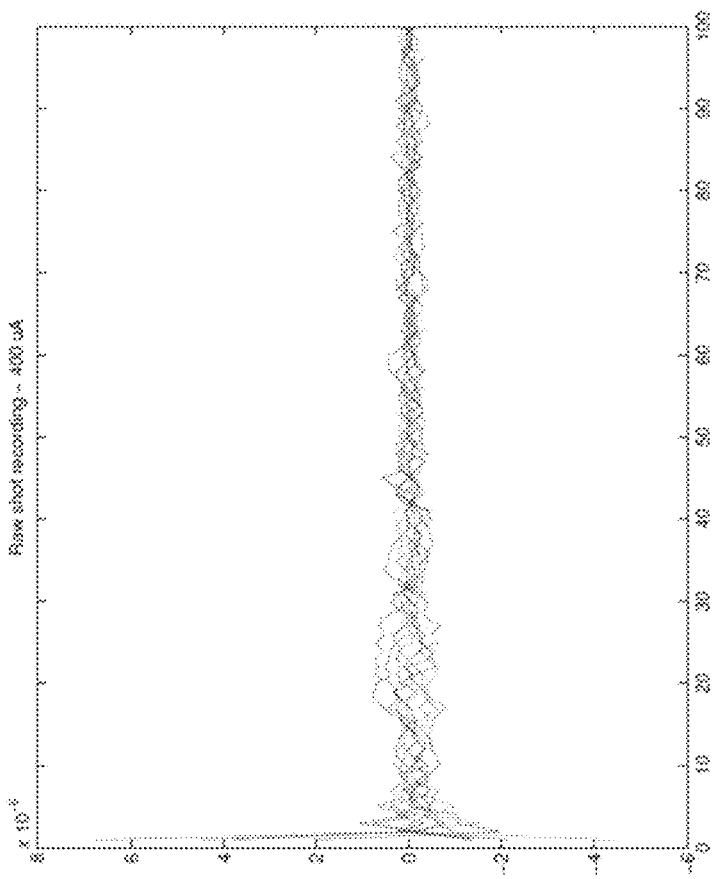
Figure 11B:
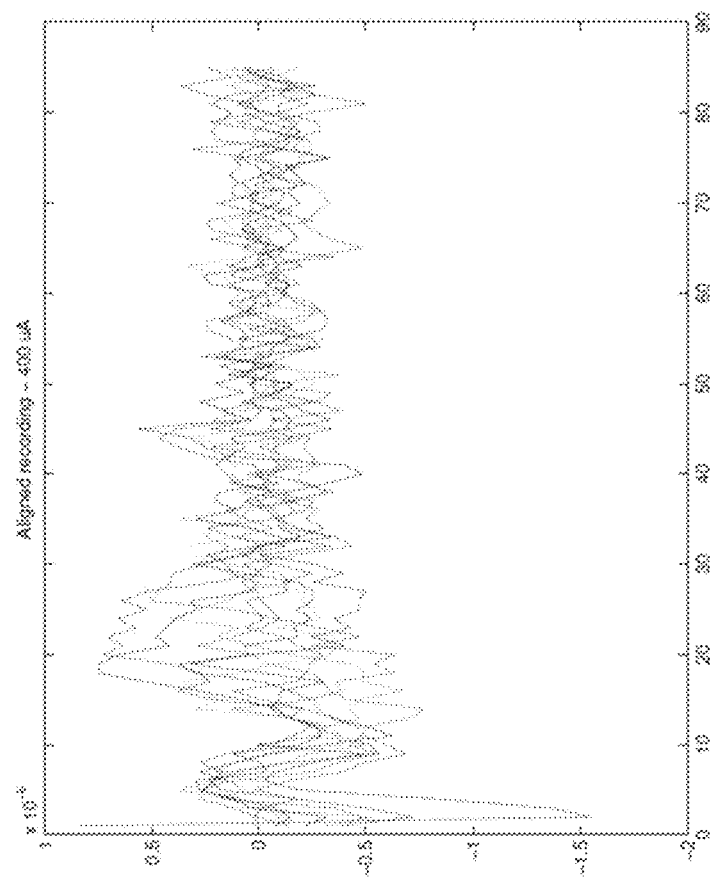
Figure 11C:
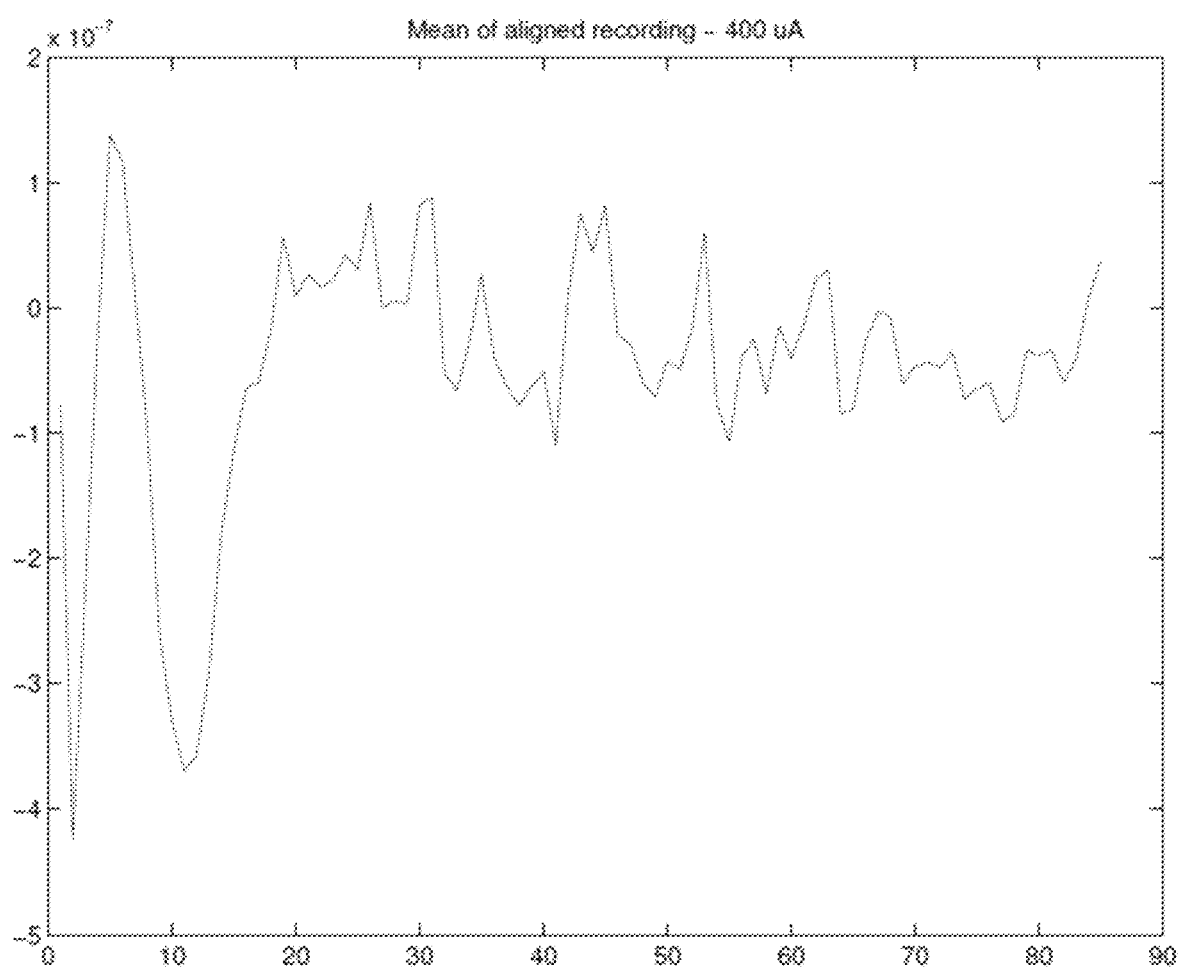
Figure 12B:
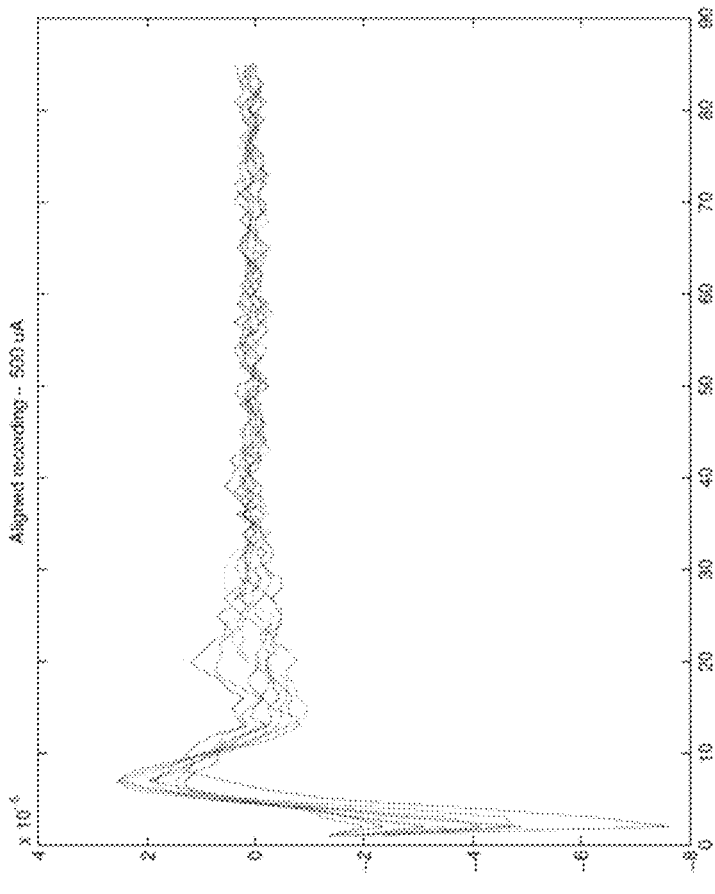
Figure 12A:
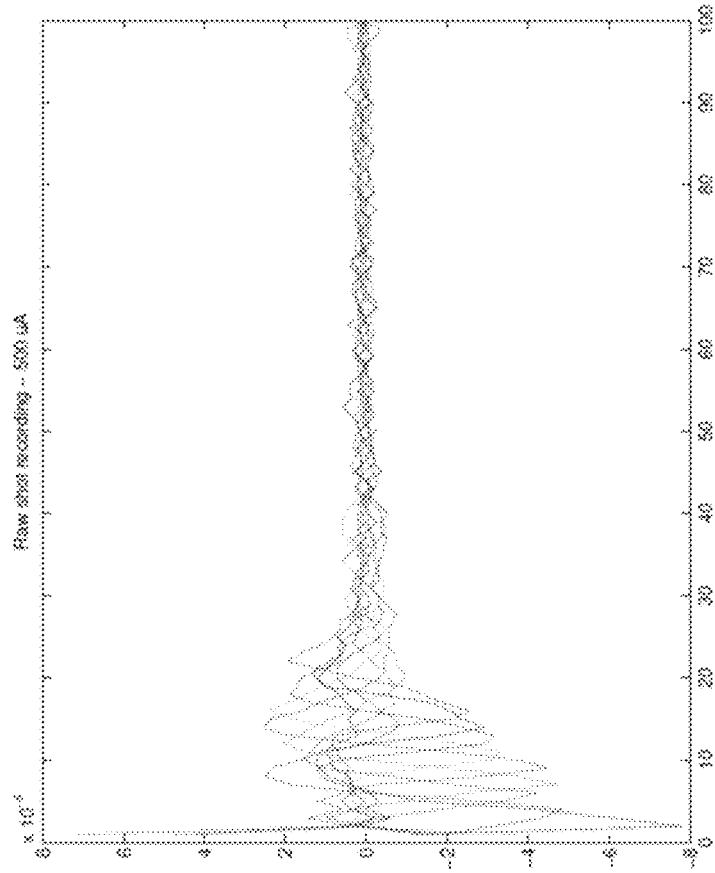
Figure 12C:
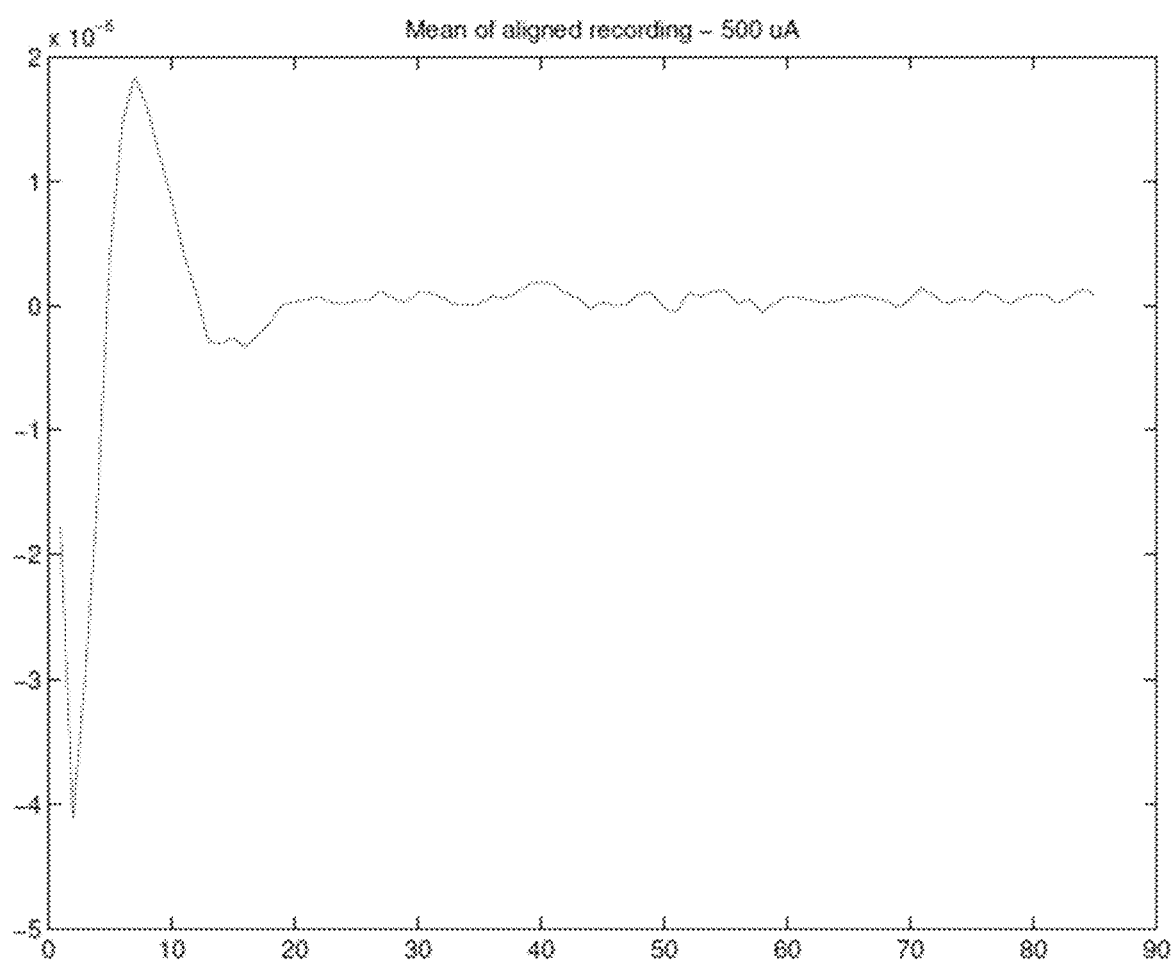

FIGS. 7-9 show data obtained by each electrode measuring a single response evoked by a single stimulus. In contrast, FIGS. 10-12 show data obtained by: application of 200 consecutive stimuli at the nominated amplitude; each electrode obtaining one recording of the response evoked by each of the 200 stimuli; and averaging the 200 recordings made by each electrode to obtain an averaged electrode recording, with the averaged electrode recordings being shown in FIGS. 10a, 11a and 12a.

Figures 8A, 8B:
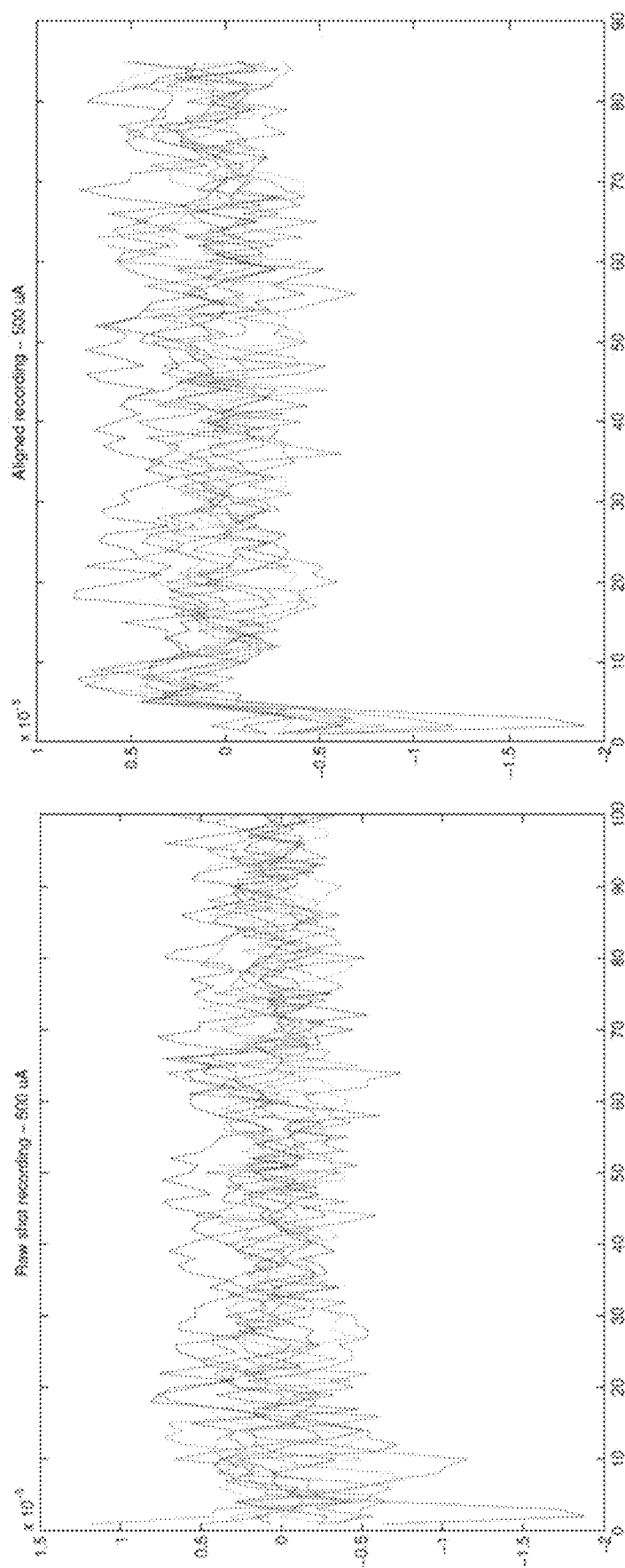
Figure 8C:
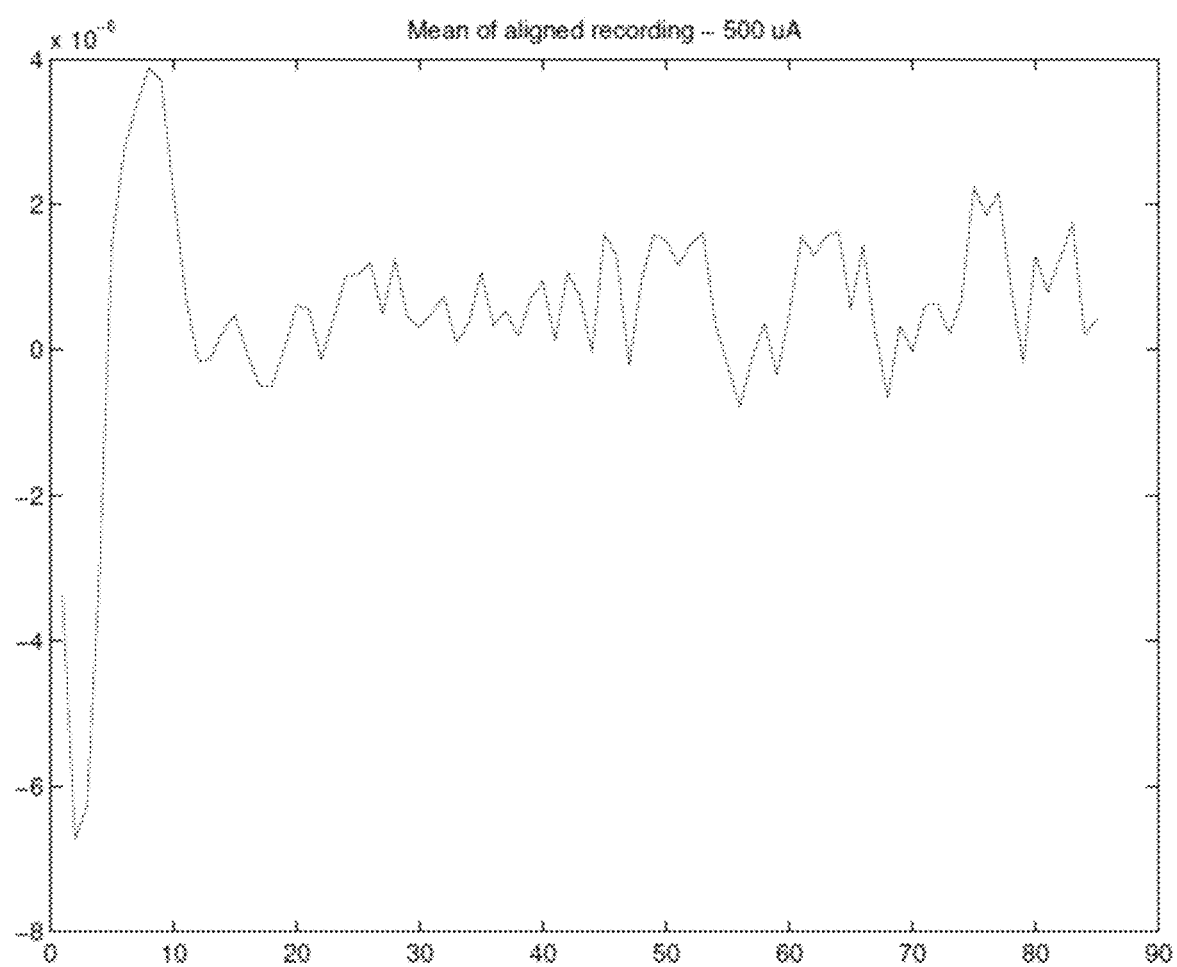
Figure 9B:
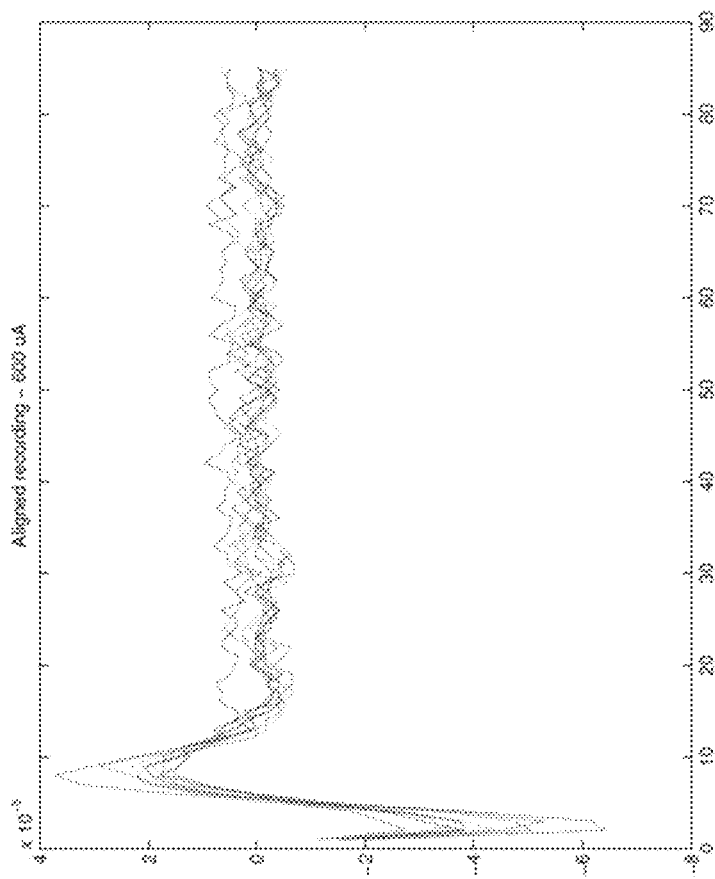
Figure 9A:
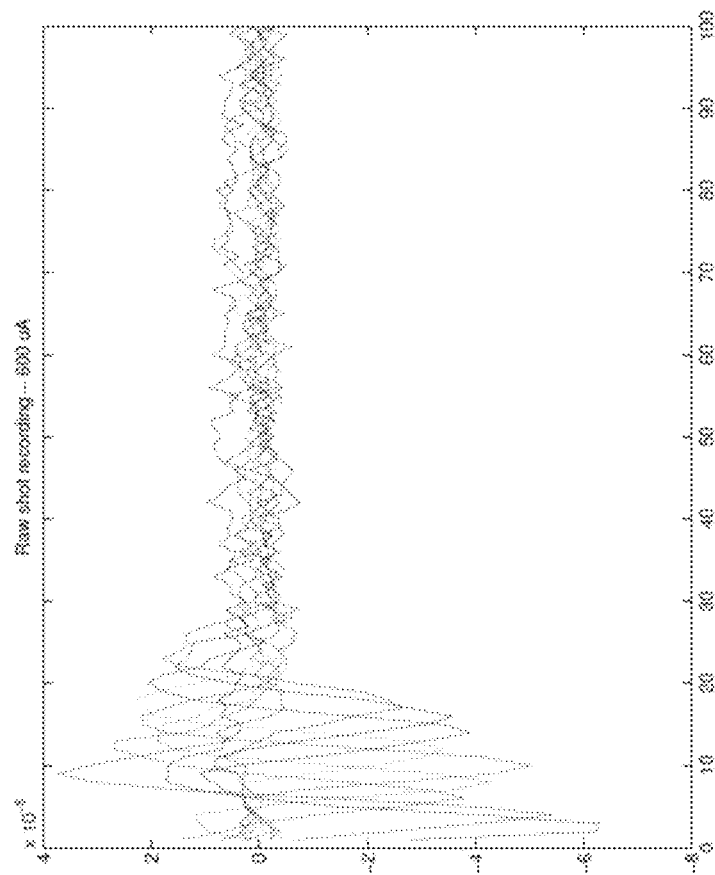
Figure 9C:
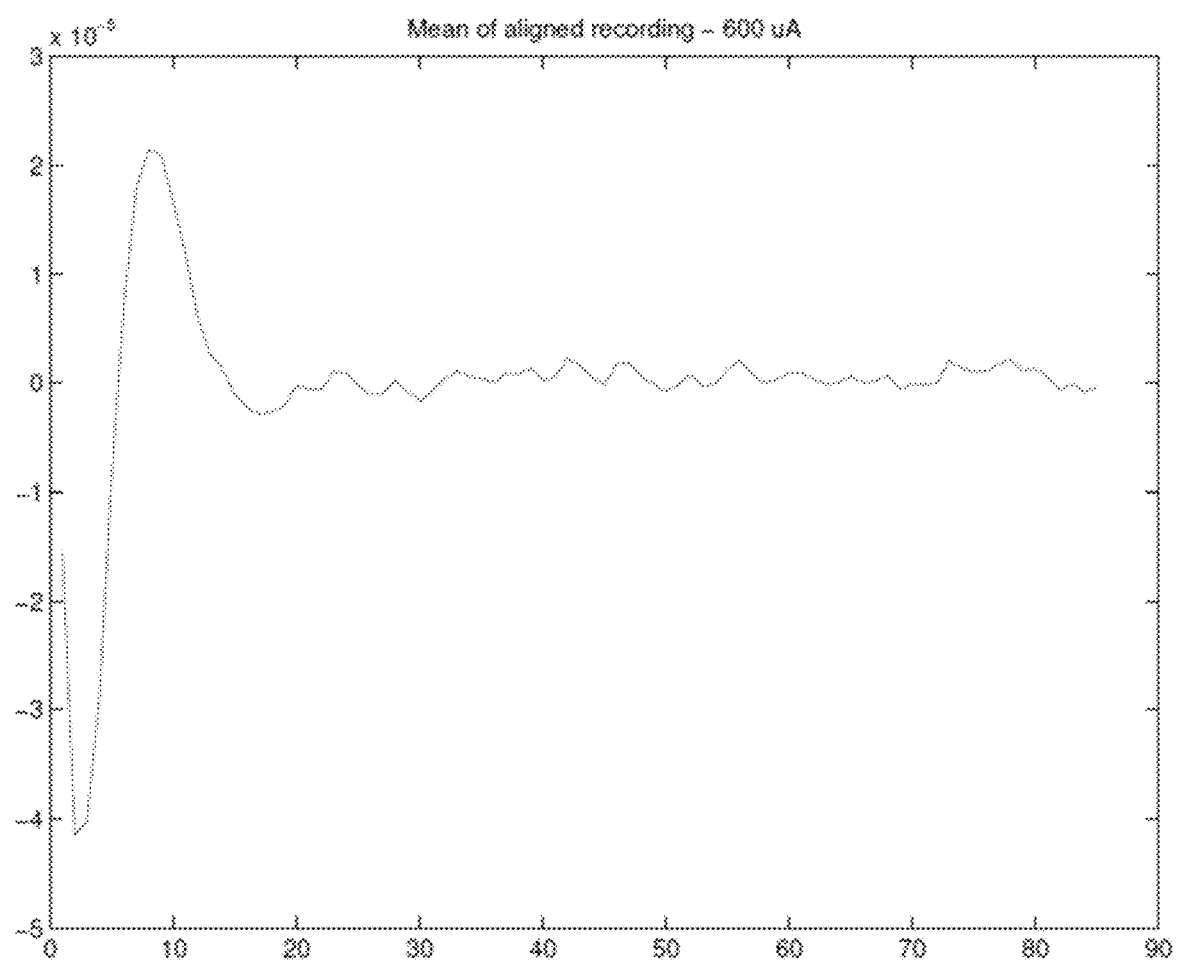

When applying the present invention to individual recordings ("shots"), FIGS. 7-9 show that an evoked response can be assessed in the aligned mean trace when stimulating at 500 µA (FIG. 8c), even though the response is not strongly evident in any of the individual electrode recordings of FIG. 8a. For the recordings over 200 shots in FIGS. 10-12, the aligned mean trace elicits the onset of neural response at an even lower stimulus level, 400 µA (FIG. 11c). This is at the expense of some latency during the time period required to obtain the 200 shots. Nevertheless in both the single-shot and 200-shot approaches the aligned mean trace makes it possible to find responses which otherwise would be indistinguishable from the sources of background noise.

Figure 3:
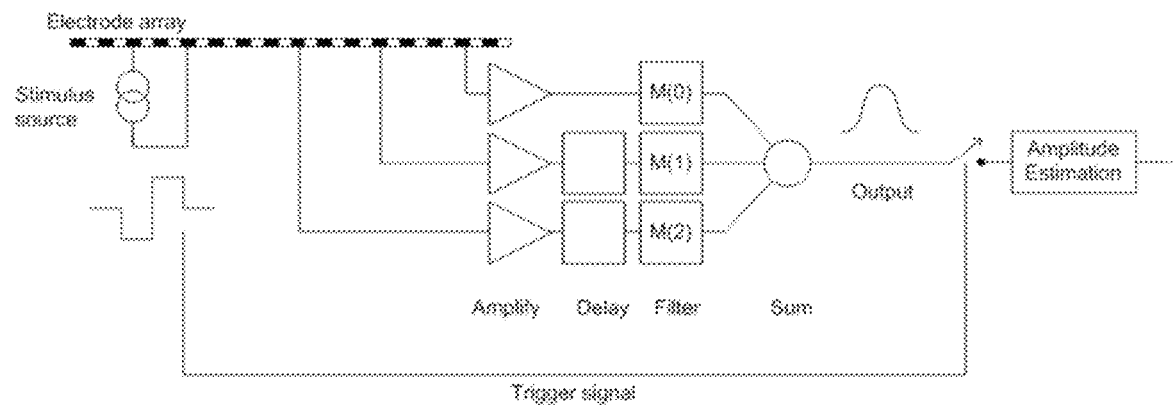
FIG. 3 illustrates another embodiment of the invention for amplifying the neural response and using a template filter.

In a further embodiment shown in FIG. 3, the gain of each amplifier is different to that of the other amplifiers, to compensate for the drop in amplitude of the neural response as it propagates along the spinal cord. Further, filters M(i) are provided for each channel which compensate for expected dispersion and spectral variation in the neural response as it travels along the spinal cord between each respective sense electrode. The embodiment of FIG. 3 thus includes delay elements to align the time-of-arrival of the signals, but also matched filters that detect the expected amplitude and wave-shape of the signal at each point. The filters may be derived in advance based on measurements of a response evoked by a high intensity stimulus, and/or based on an average of multiple measurement cycles, in order to improve signal to noise ratio. The filter may also be defined in a manner to include the delay. The output, having a band-limited impulse shape, is then suitable for sampling and amplitude estimation, and can be used in a feedback loop. The time of the expected peak in the summation output is known from the geometry of the electrode array, and the (known) distance from the stimulating electrode to the sense electrode, or a delay $t_n$ for the nth sense electrode may be empirically estimated as discussed previously herein. Once again, this architecture of FIG. 3 improves the apparent SNR of the system compared to that of individual amplifiers, because the amplifier noise signals are not correlated. It will also improve SNR because the matched filter integrates the cross correlation of the signal and the filter impulse response (a template), providing coding gain. Preamble detection techniques may thus be applied in this and other embodiments of the invention.

Figure 4:
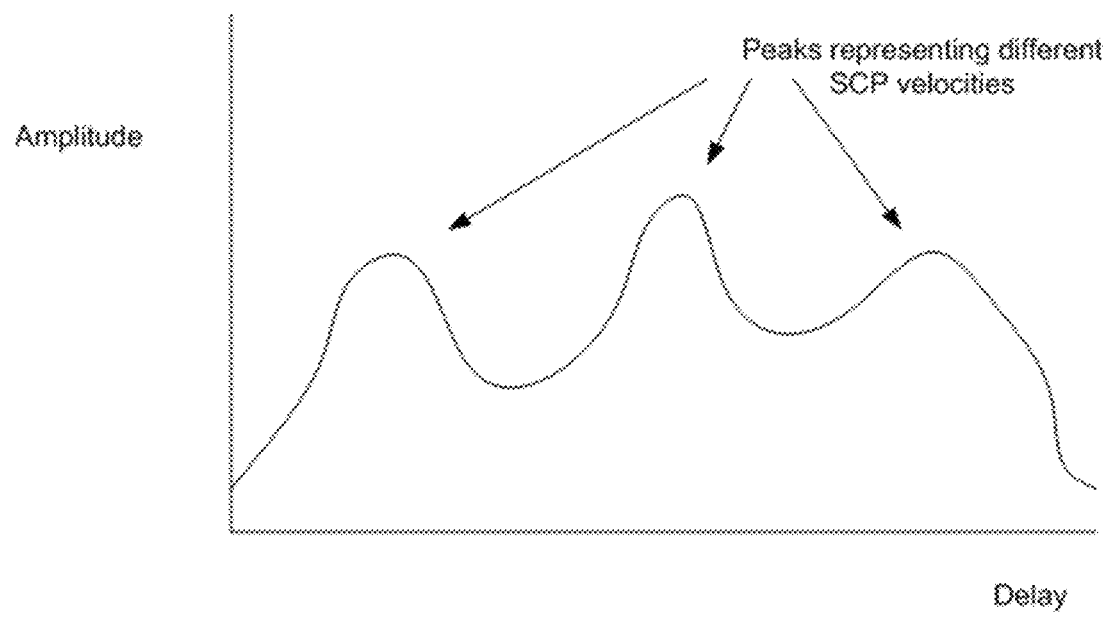
FIG. 4 is a plot of a propagram illustrating the relationship between t and the output amplitude.

If the delay t is varied while recording the amplitude of the SCP response, then the relationship between t and the output amplitude can be plotted as a "propagram", as illustrated in FIG. 4. The propagram has peaks representing the responses of the different fibre classes. The amplitude and/or position of each peak can be used as the basis of a feedback loop, for example to control selectivity of the fibre class corresponding to that peak. More complex calculations may also be based on the peaks, such as the ratio of two peak amplitudes. The relationship between t and another SCP characteristic, such as response energy, could be similarly assessed.

The position of each peak in the propagram of FIG. 4 may also be used to measure propagation velocity of the respective fibre class.

As the signal propagates down a spinal cord it reduces in amplitude and disperses. Accordingly, the configuration of FIG. 2 may be refined to give the amplifier elements associated with each respective electrode different gain values and/or phase terms to mimic the attenuation and spreading. Moreover, filters may be introduced in each signal chain which are matched to the expected neural response sensed by that respective electrode, so that by accumulating the filter output a measure of the amplitude of the response can be obtained. Indeed, alternative embodiments may utilise a template generator, multiplier and accumulator bank instead of an ADC, giving simpler device fabrication and coding gain. Where it is known the time at which the signal starts, only a single accumulator would be required, although for unknown stimuli onset (for example in response to stimulation at the periphery) multiple accumulators may be required.

Figure 5:
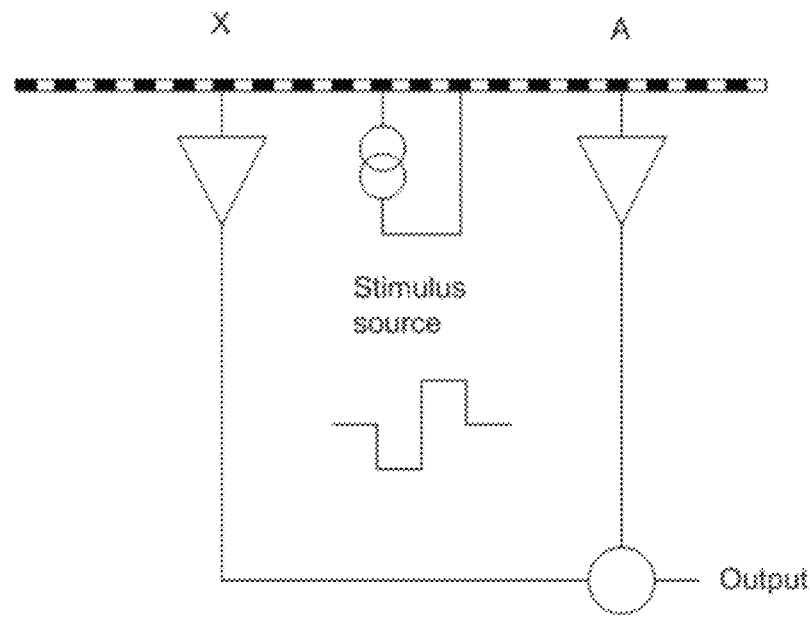
FIG. 5 illustrates another embodiment in which the first and second recordings are obtained from either side of a stimulus.
Figure 6:
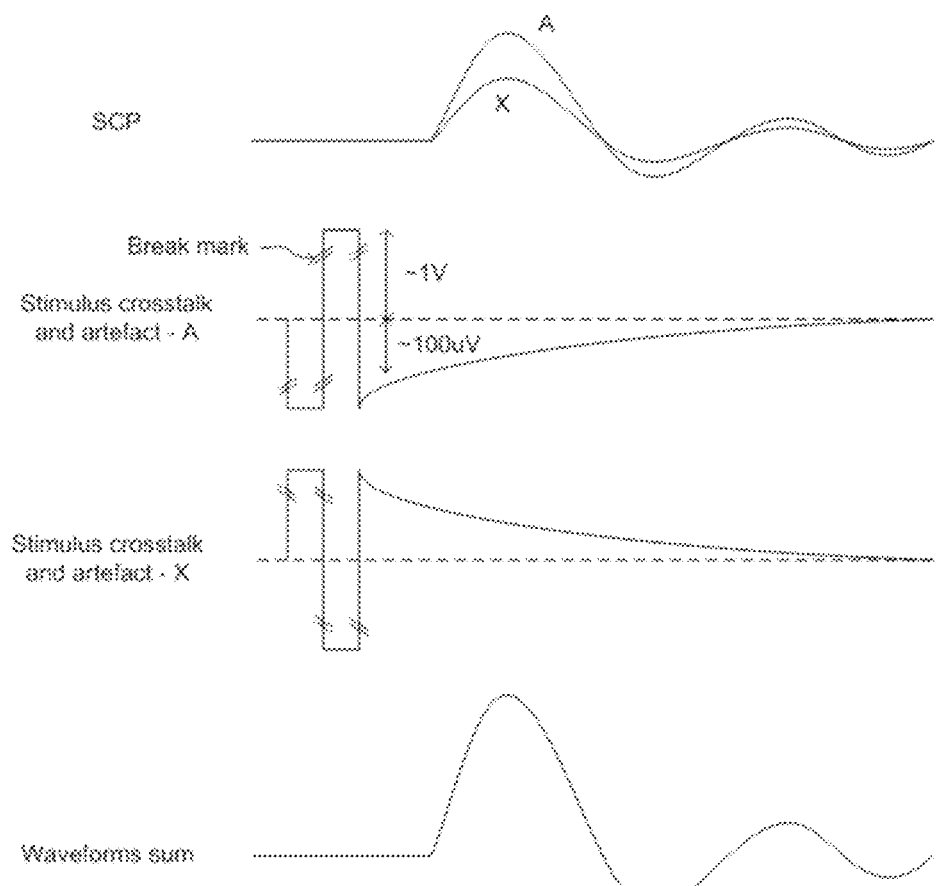
FIG. 6 illustrates the artefact cancellation effect of the measurement technique of FIG. 5.

A further variant is shown in FIG. 5, in which the stimulus is presented by an electrode in the middle of an array, with sense electrodes and measurement amplifiers on either side. The signals obtained from the amplifiers are shown FIG. 6. The SCPs are of similar amplitude, and similar delay from the time of stimulus. There can be variations in amplitude due to certain effects, such as the distance of the electrode from the spinal cord, but the signals are largely the same. The electrode crosstalk and artefact are also shown. A "break mark" is used so that this single plot can show both the stimulus crosstalk (having amplitude of typically 1V) and the artefact (having amplitude typically of the order of 100 µV). Importantly, the respective stimulus crosstalk artefacts received at the sense electrodes are of opposite polarity, whereas the SCPs are of the same polarity. Consequently, in the output signal formed from the sum of the signals obtained from the electrodes on either side of the stimulus electrode, the crosstalk and artefact will cancel, while the SCP will sum.

While FIG. 5 shows the measurement electrodes being caudorostrally positioned relative to the stimulus electrode, it is to be noted that in an electrode array having 3 or more columns of electrodes, the measurement electrodes may be positioned laterally of the stimulus electrode(s). In another arrangement, a single sense electrode may be positioned between the stimulus electrodes whereby the stimulus artefact will cancel or be attenuated at that centrally positioned sense electrode.

These embodiments thus recognise that each node of Ranvier of a nerve fibre acts as a current source expressing an action current which is fixed for a given diameter. Each node's action current is delayed with respect to the previous node (closer to the initiation) but not otherwise different. The nodes each act as a point source within a volume conductor, and consequently the recording at each electrode can be considered to be a weighted summation of all action currents via a spatial transimpedance function. The recorded system can in turn be modelled as a line current source, along which an action current translates; and the variation in conduction velocities represents a dispersion of the action current in space (and consequently time). Thus, each subsequent electrode's recording is a delayed and dispersed version of a nearer electrode's recording. By applying an inverse delay to each electrode's signal, the travel delay and the weighted mean of the dispersion delays can be cancelled. These signals can then be averaged, which reduces synchronous and uncorrelated noise, while retaining the portion of the signal that represents the travelling character.

In alternative embodiments, delayed-sum recordings which allow sufficient improvements in signal to noise ratio may permit use of implanted or skin-surface electrodes. Delayed-sum recordings may be made for either evoked or non-evoked potentials. Delayed sum recordings can be made in any part of the body where a signal is known to propagate according to a known path.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A device for measuring a neural response evoked by a neural stimulus, the device comprising:
   at least a first sense electrode and a second sense electrode, the first and second sense electrodes being configured to be positioned at distinct locations along a neural pathway;
   a first measurement amplifier circuit configured to amplify signals from the first sense electrode;
   a second measurement amplifier circuit configured to amplify signals from the second sense electrode; and
   a control unit configured to apply the neural stimulus, the control unit further configured to make a first recording of a first compound action potential evoked by the neural stimulus, the first recording being made using the first measurement amplifier circuit and the first sense electrode, the control unit further configured to make, simultaneously with the first recording, a second recording of the first compound action potential evoked by the stimulus, the second recording being made using the second measurement amplifier circuit and the second sense electrode;
   wherein the first measurement amplifier circuit has a first transfer function and the second measurement amplifier circuit has a second transfer function, and wherein the second transfer function differs from the first transfer function in a manner corresponding to a variation in the first compound action potential as the first compound action potential travels between the first sense electrode and the second sense electrode.

2. The device of claim 1, wherein a gain of the first transfer function of the first measurement amplifier circuit is different to a gain of the second transfer function of the second measurement amplifier circuit, in a manner which compensates for a drop in amplitude of the first compound action potential as the first compound action potential travels between the first sense electrode and the second sense electrode.

3. The device of claim 1 wherein at least one of the first measurement amplifier circuit and the second measurement amplifier circuit further comprises a matched filter matched to a response and which compensates for dispersion and spectral variation in the first compound action potential as the first compound action potential travels between the first sense electrode and the second sense electrode.

4. The device of claim 2, wherein at least one of the first measurement amplifier circuit and the second measurement amplifier circuit further comprises a matched filter which compensates for dispersion and spectral variation in the first compound action potential as the first compound action potential travels between the first sense electrode and the second sense electrode.

5. The device of claim 1, where the first and second electrode are a distance d apart and a selected neural fibre class has a conduction velocity of c, and wherein the control unit is further configured to delay the first recording by a time period $t=d/c$ to produce a delayed first recording and wherein the control unit is further configured to compare the delayed first recording with the second recording.

6. The device of claim 1, wherein the control unit is configured to sum together the first recording and the second recording.

7. The device of claim 1, wherein the control unit is further configured to obtain more than two recordings from respective electrodes spaced apart along the neural pathway.

8. The device of claim 1, wherein the control unit is further configured to apply phase terms to each of the first recording and the second recording, to compensate for dispersion of the first compound action potential along the neural pathway.

* * * * *